(12) United States Patent
Bouduban et al.

(10) Patent No.: US 11,793,506 B2
(45) Date of Patent: Oct. 24, 2023

(54) SUTURE ANCHOR SYSTEM AND METHOD

(71) Applicant: DePuy Synthes Products, Inc., Raynham, MA (US)

(72) Inventors: Nicolas Bouduban, Oberdorf (CH); Patrick Burki, Oberdorf (CH); Beat Lechmann, Oberdorf (CH); Philippe Gedet, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 90 days.

(21) Appl. No.: 17/347,132

(22) Filed: Jun. 14, 2021

(65) Prior Publication Data

US 2021/0369262 A1 Dec. 2, 2021

Related U.S. Application Data

(62) Division of application No. 16/149,341, filed on Oct. 2, 2018, now Pat. No. 11,033,259, which is a division
(Continued)

(51) Int. Cl.
*A61B 17/04* (2006.01)

(52) U.S. Cl.
CPC ...... *A61B 17/0401* (2013.01); *A61B 17/0483* (2013.01); *A61B 2017/042* (2013.01); *A61B 2017/0403* (2013.01); *A61B 2017/0409* (2013.01); *A61B 2017/0412* (2013.01); *A61B 2017/0414* (2013.01); *A61B 2017/0441* (2013.01); *A61B 2017/0445* (2013.01)

(58) Field of Classification Search
CPC ............ A61B 17/0401; A61B 17/0483; A61B 2017/0403; A61B 2017/0409; A61B 2017/0412; A61B 2017/0414; A61B 2017/042; A61B 2017/0441; A61B 2017/0445
See application file for complete search history.

(56) References Cited

U.S. PATENT DOCUMENTS 2,856,933 A 10/1958 Hildebrand et al.
4,779,616 A 10/1988 Johnson
(Continued)

FOREIGN PATENT DOCUMENTS

CN 101321498 12/2008
EP 1 199 035 4/2002
(Continued)

OTHER PUBLICATIONS

International Search Report and Written Opinion (PCT/US2012/040916); dated Nov. 7, 2012.
(Continued)

*Primary Examiner* — Sarah A Long
(74) *Attorney, Agent, or Firm* — Dunlap Codding, P.C.

(57) ABSTRACT

A suture anchor method including a suture anchor and a suture anchor drive. The suture anchor is positionable on a rod of the suture anchor drive. The rod defines an awl for forming a hole in a bone. The suture anchor drive further has an impactor for moving the suture anchor along the rod between a retracted position and an advanced position so as to implant the suture anchor in the bone with the awl positioned in the bone.

5 Claims, 25 Drawing Sheets

Related U.S. Application Data of application No. 13/488,893, filed on Jun. 5, 2012, now Pat. No. 10,092,284.

(60) Provisional application No. 61/605,978, filed on Mar. 2, 2012, provisional application No. 61/500,433, filed on Jun. 23, 2011.

(56) References Cited

U.S. PATENT DOCUMENTS

| | | | |
|---|---|---|---|
| 4,946,468 A | 8/1990 | Li | |
| 4,968,315 A | 11/1990 | Gatturna | |
| 5,002,550 A | 3/1991 | Li | |
| 5,171,314 A | 12/1992 | Dulebohn | |
| 5,217,486 A | 6/1993 | Rice et al. | |
| 5,334,204 A | 8/1994 | Clewett et al. | |
| 5,501,692 A | 3/1996 | Riza | |
| 5,522,845 A | 6/1996 | Wenstrom, Jr. | |
| 5,690,676 A | 11/1997 | DiPoto et al. | |
| 5,697,950 A | 12/1997 | Fucci et al. | |
| 5,707,395 A | 1/1998 | Li | |
| 5,782,864 A | 7/1998 | Lizardi | |
| 5,800,447 A | 9/1998 | Wenstrom, Jr. | |
| 5,906,624 A | 5/1999 | Wenstrom, Jr. | |
| 6,508,830 B2 | 1/2003 | Steiner | |
| 6,527,795 B1 | 3/2003 | Lizardi | |
| 6,544,281 B2 | 4/2003 | ElAttrache et al. | |
| 6,641,596 B1 | 11/2003 | Lizardi | |
| 6,692,516 B2 | 2/2004 | West, Jr. et al. | |
| 6,733,506 B1 | 5/2004 | McDevitt et al. | |
| 7,083,638 B2 | 8/2006 | Foerster | |
| 7,217,279 B2 | 5/2007 | Reese | |
| 7,517,357 B2 | 4/2009 | Abrams et al. | |
| 7,588,587 B2 | 9/2009 | Barbieri et al. | |
| 7,618,462 B2 | 11/2009 | Ek | |
| 7,753,917 B2 | 7/2010 | Urbanski et al. | |
| 7,803,173 B2 | 9/2010 | Burkhart et al. | |
| 7,963,972 B2 | 6/2011 | Foerster et al. | |
| 7,981,140 B2 | 7/2011 | Burkhart | |
| 8,460,340 B2 | 6/2013 | Sojka et al. | |
| 2001/0041916 A1 | 11/2001 | Bonutti | |
| 2006/0253119 A1* | 11/2006 | Berberich | A61B 17/0401 606/232 |
| 2006/0276841 A1* | 12/2006 | Barbieri | A61B 17/0401 606/232 |
| 2008/0140118 A1 | 6/2008 | Martinek | |
| 2008/0215091 A1 | 9/2008 | Dreyfuss | |
| 2008/0306511 A1 | 12/2008 | Cooper et al. | |
| 2009/0088798 A1 | 4/2009 | Snyder et al. | |
| 2009/0234387 A1 | 9/2009 | Miller et al. | |
| 2009/0312794 A1 | 12/2009 | Nason et al. | |
| 2010/0004683 A1 | 1/2010 | Hoof et al. | |
| 2010/0152773 A1 | 6/2010 | Lunn et al. | |
| 2011/0004247 A1 | 1/2011 | Lechmann et al. | |

FOREIGN PATENT DOCUMENTS

| | | |
|---|---|---|
| EP | 2 186 486 | 5/2010 |
| JP | 2007/075616 | 3/2007 |
| JP | 2007/307379 | 11/2007 |
| JP | 2007/532269 | 11/2007 |
| JP | 2008/535544 | 9/2008 |
| JP | 2010/131428 | 6/2010 |
| JP | 2010/537697 | 12/2010 |
| WO | 01/30253 | 5/2001 |
| WO | 2004/075777 | 9/2004 |
| WO | 2006/099109 | 9/2006 |
| WO | 2010/028324 | 3/2010 |
| WO | 2010/065274 | 6/2010 |

OTHER PUBLICATIONS

Notification of Reasons of Refusal (Japanese Patent Application No. 2014/516988); dated Mar. 22, 2016.

\* cited by examiner

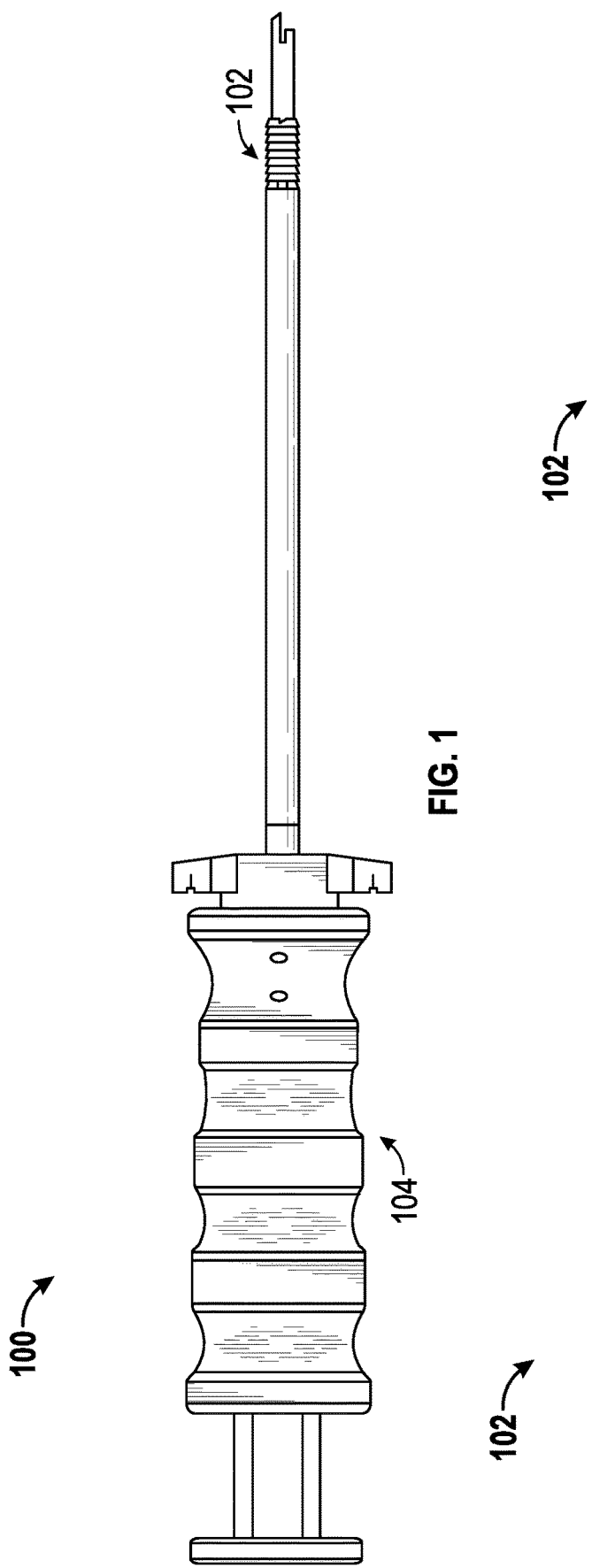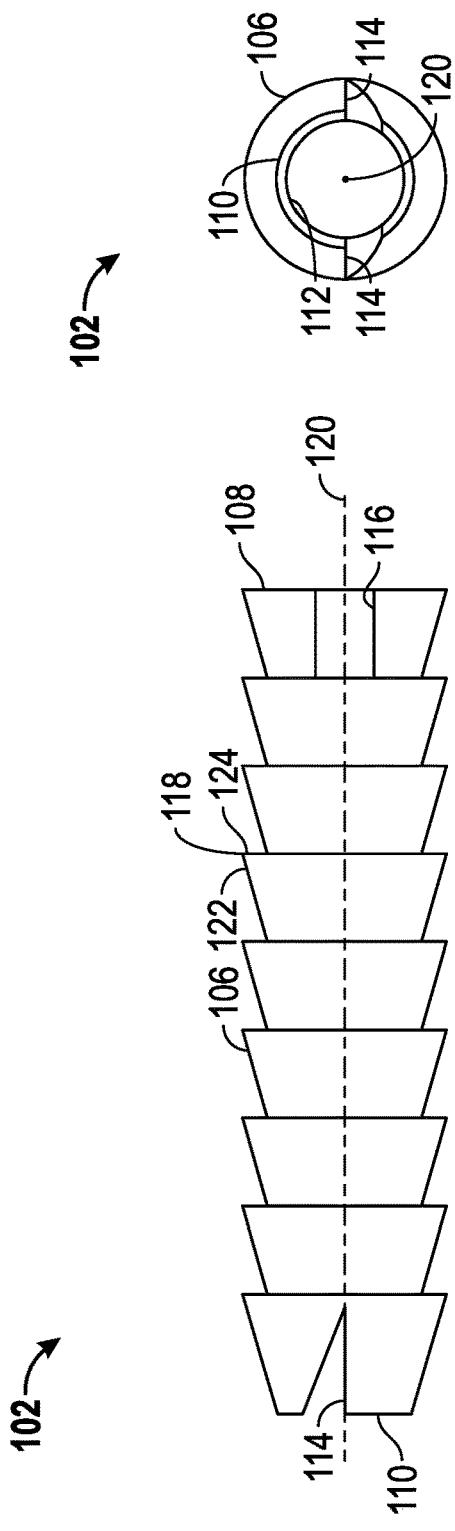

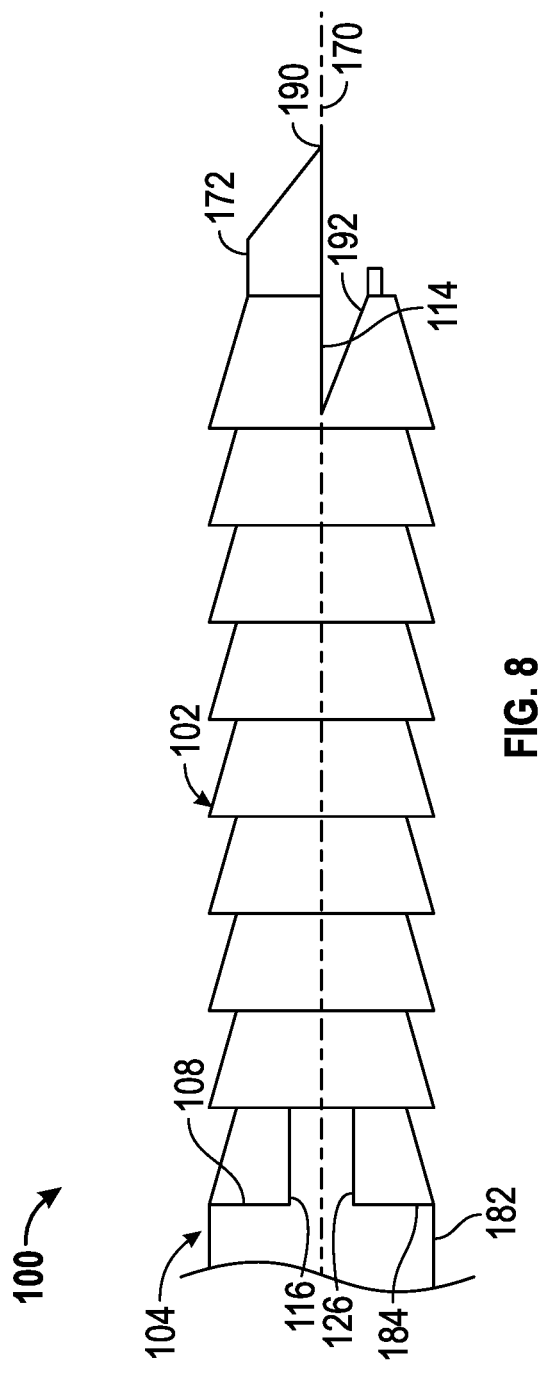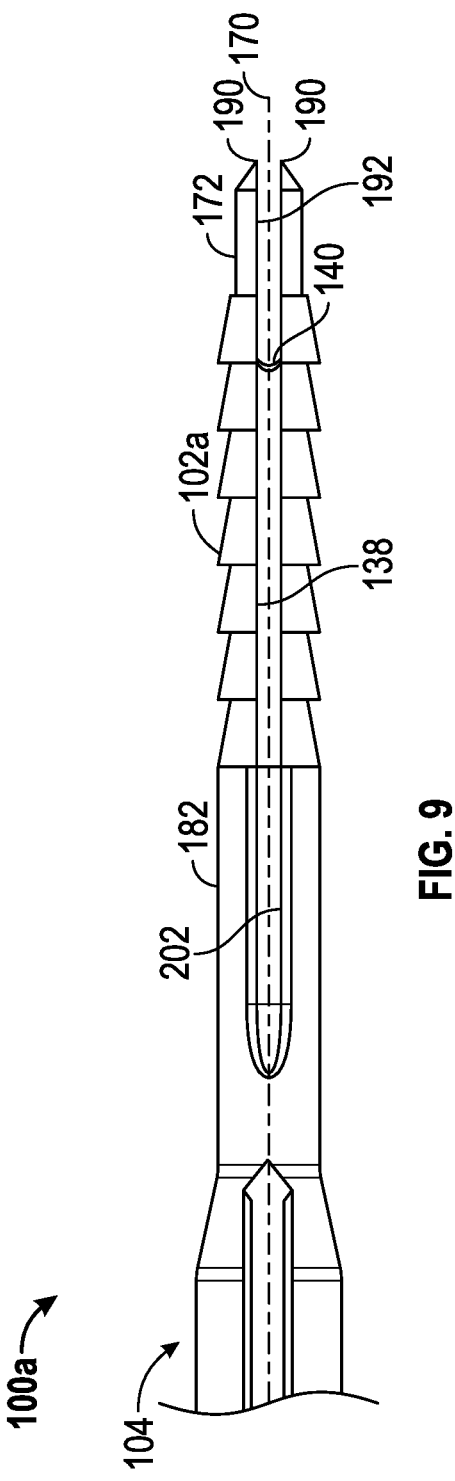

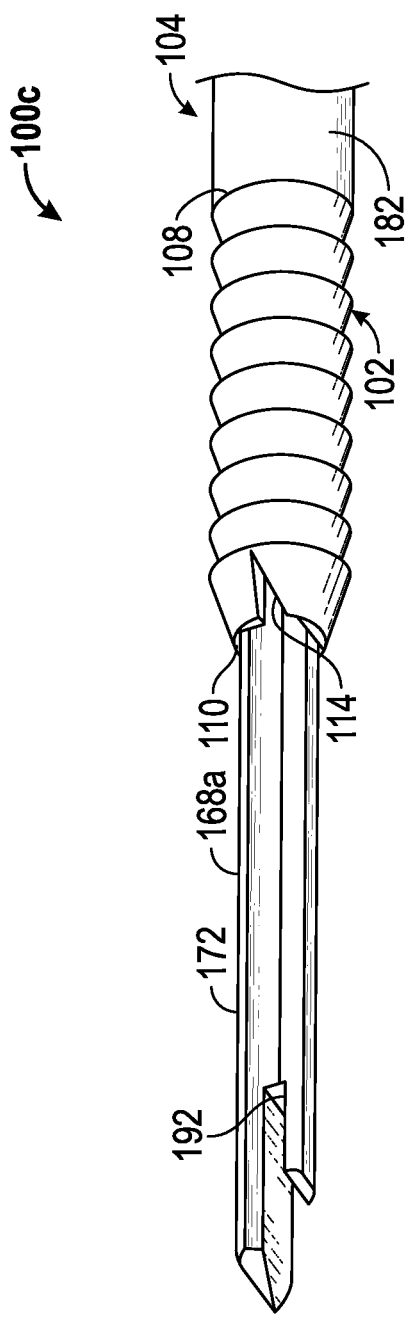
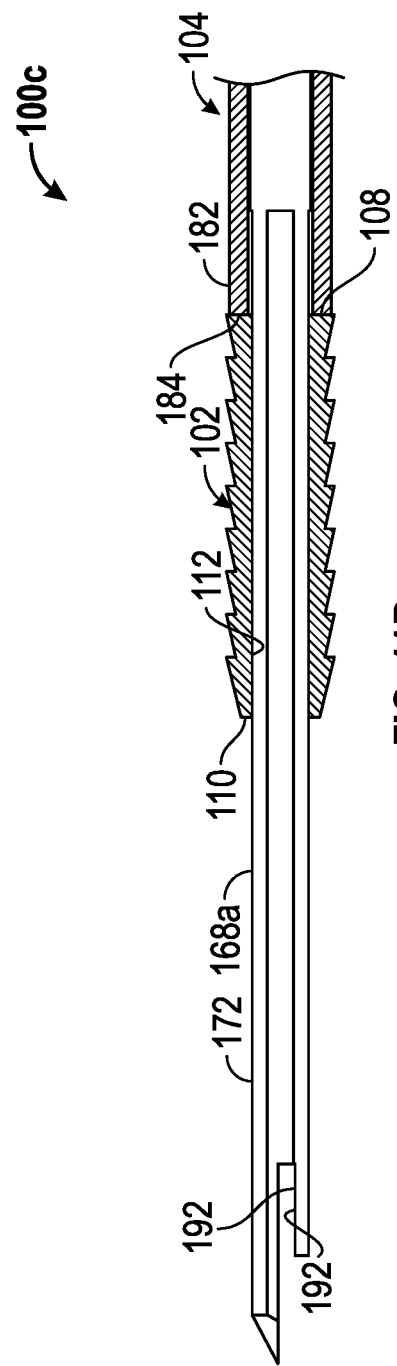

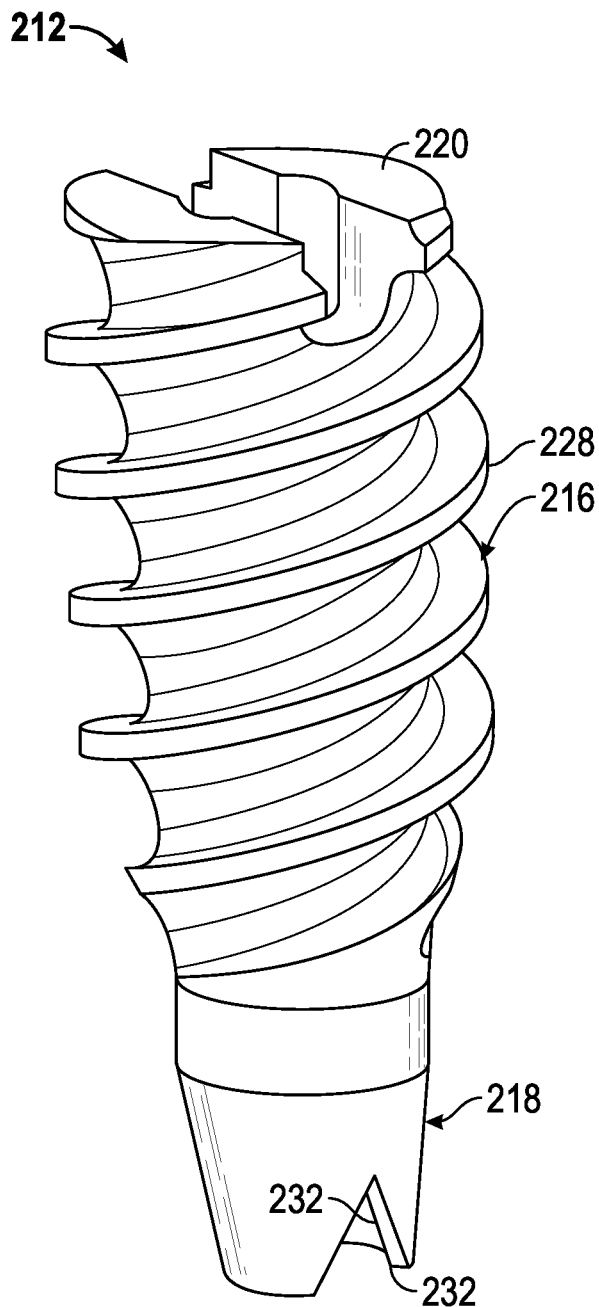
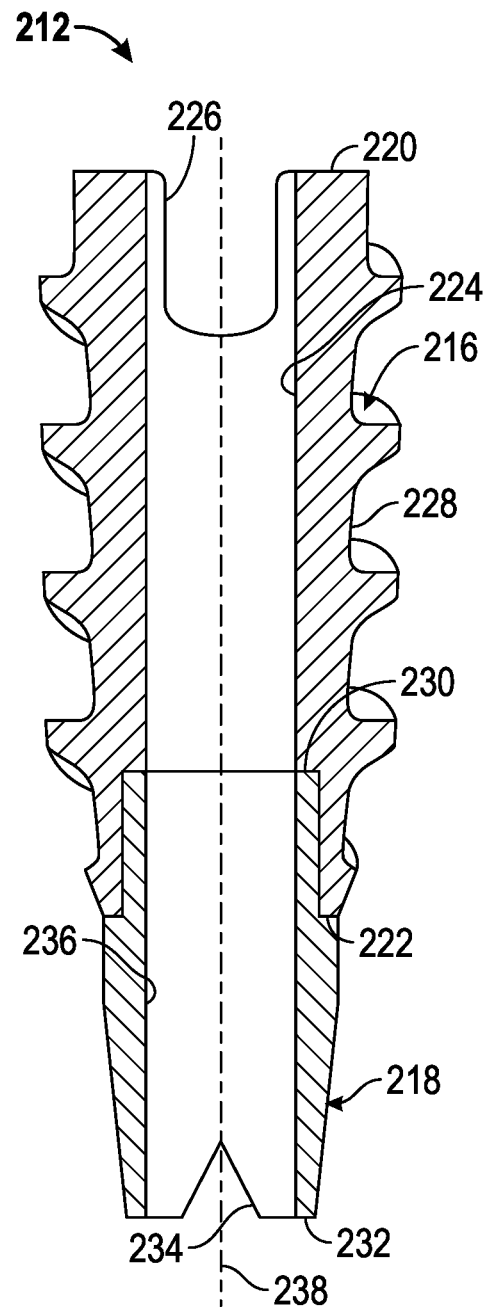
FIG. 16     FIG. 17

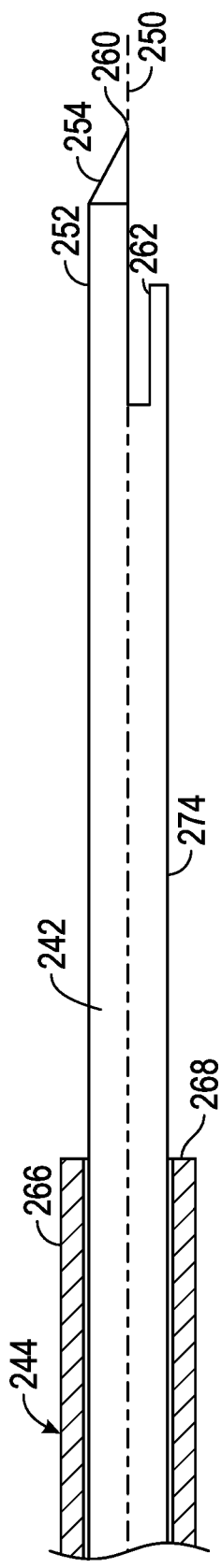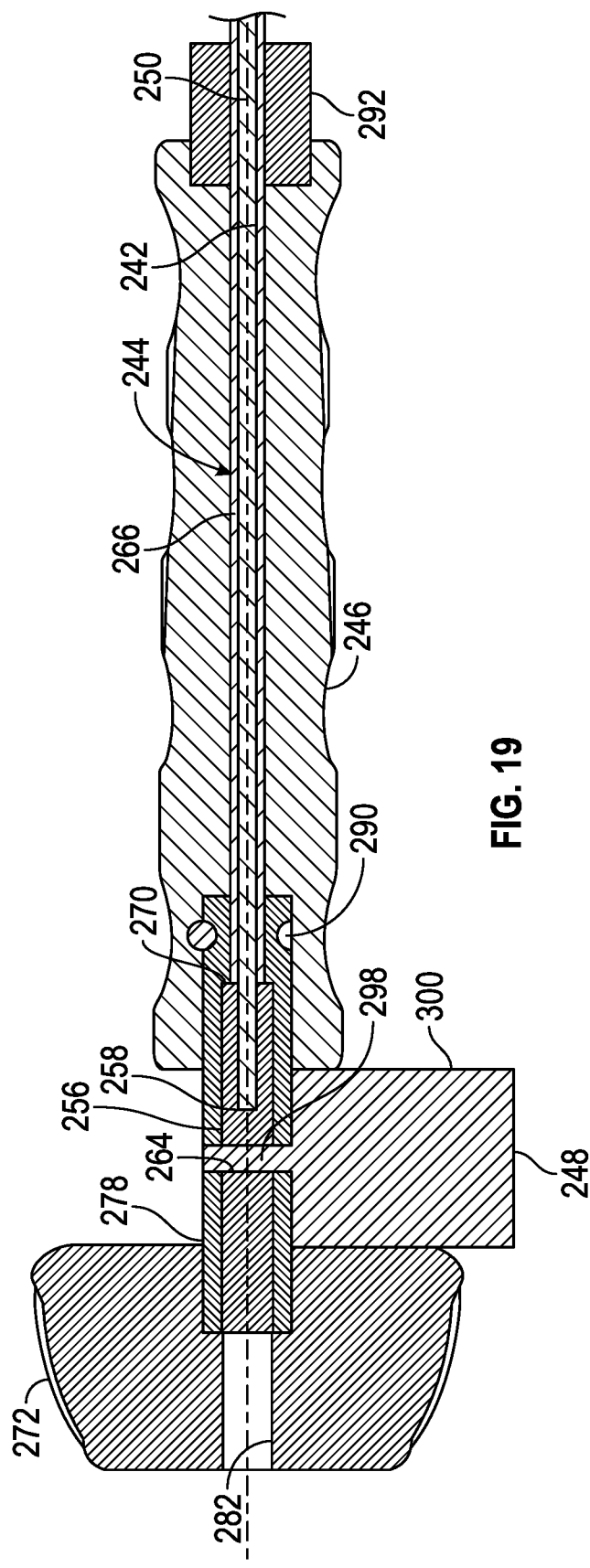

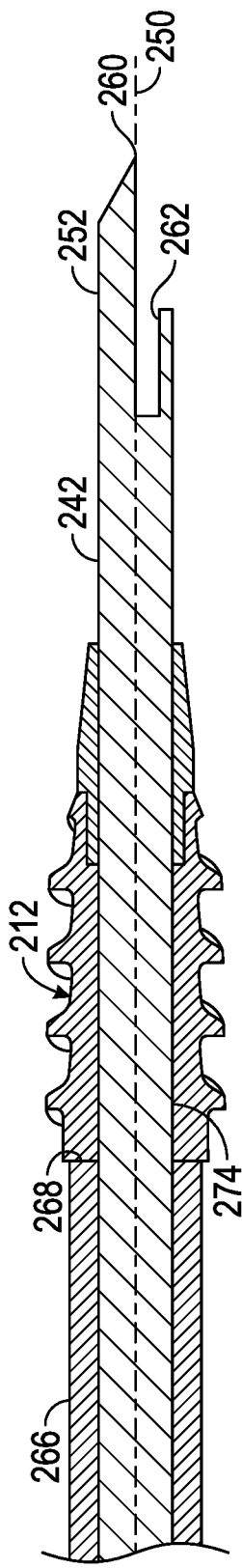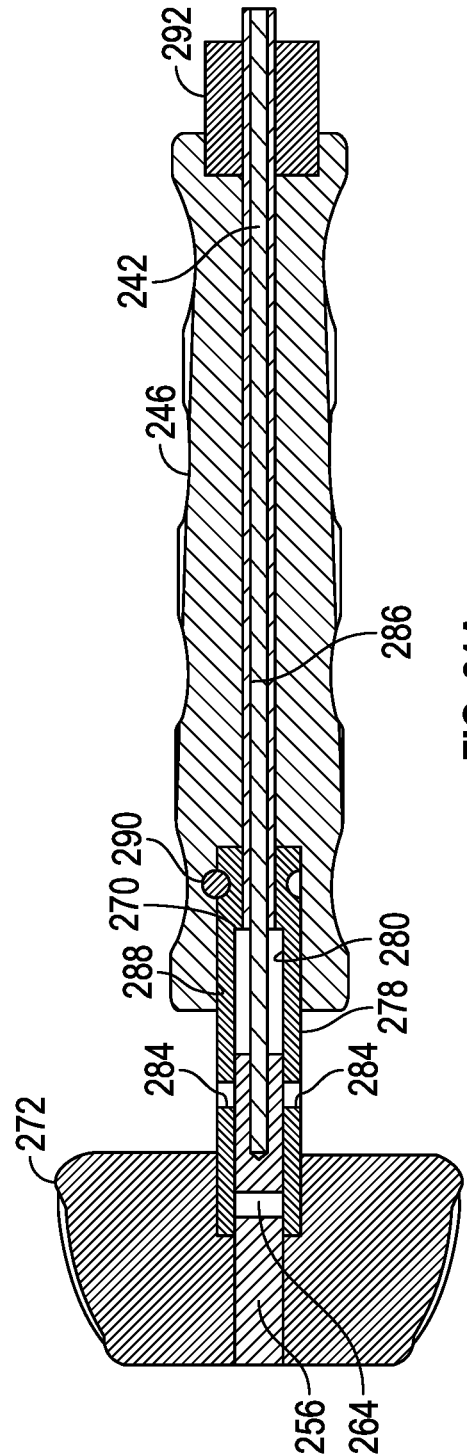
FIG. 20
FIG. 21A

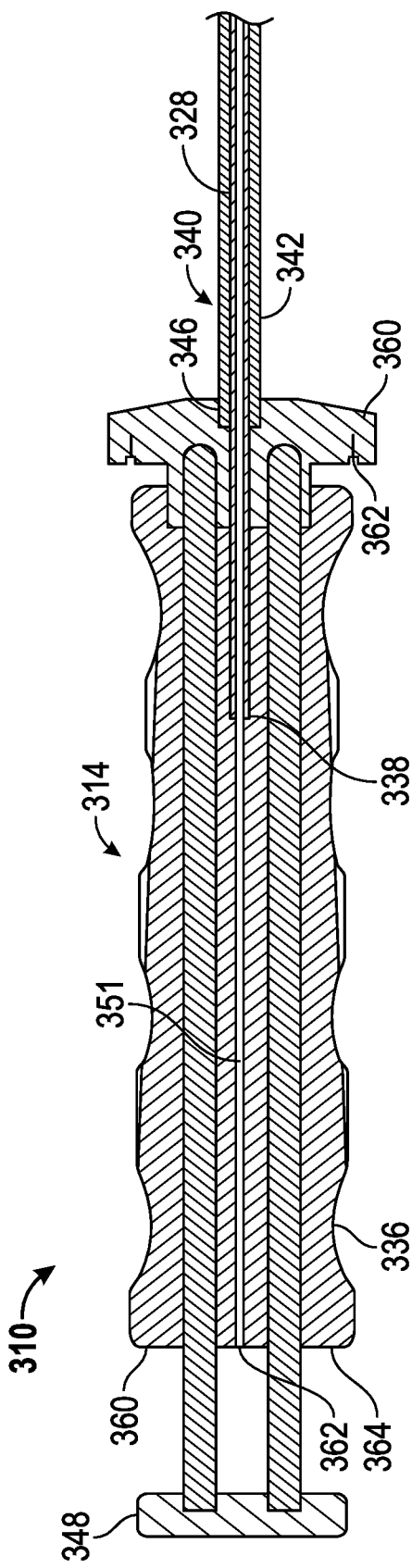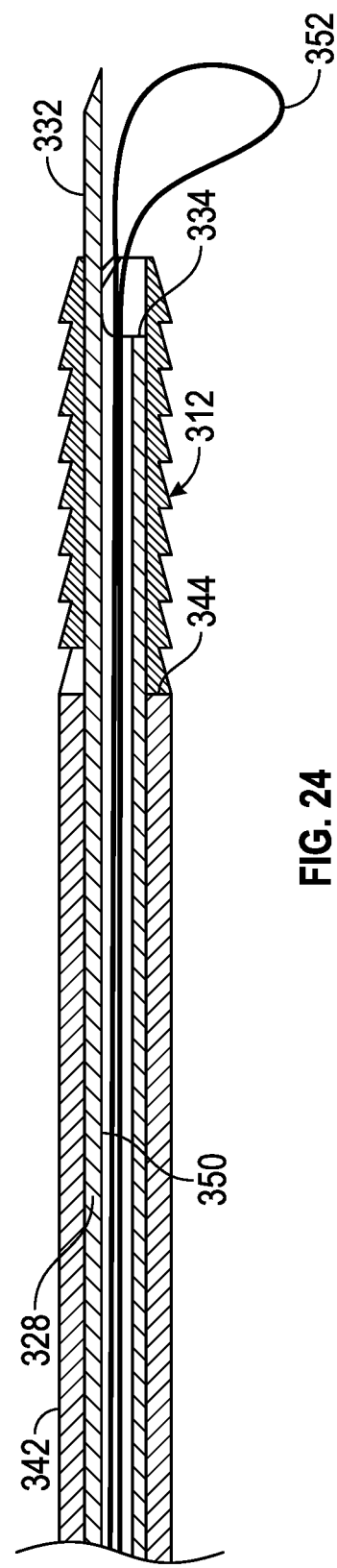
FIG. 23
FIG. 24

SUTURE ANCHOR SYSTEM AND METHOD

CROSS-REFERENCE TO RELATED APPLICATIONS

This application is a divisional of U.S. patent application Ser. No. 16/149,341, filed Oct. 2, 2018, which is a divisional of U.S. Ser. No. 13/488,893, filed Jun. 5, 2012, now U.S. patent Ser. No. 10/092,284, which claims priority to U.S. Provisional Application Ser. No. 61/500,433, filed on Jun. 23, 2011, and to U.S. Provisional Application Ser. No. 61/605,978, filed on Mar. 2, 2012, the entire contents of each being hereby expressly incorporated herein by reference.

BACKGROUND

Soft tissues, such as tendons and ligaments, generally are attached to bone by small collagenous fibers. These fibers are strong, but permit the tendons and ligaments to be flexible. When soft tissue is torn away from the bone and requires repair, a surgeon is often required to repair the detached soft tissue with sutures which are attached to the bone by an anchor. These anchors are usually implanted into a patient's bone through extensive surgical procedures and more recently, through arthroscopic surgical techniques. Existing anchors are implanted into a patient's bone in a number of ways, which can generally be classified as those that require drilling of a hole in the bone, and those that can be implanted without drilling, such as pushed-in or screwed-in the bone, for example.

Once an anchor is implanted in a bone, a suture is typically passed through the soft tissue to be reattached, which suture is then secured to the anchor at the appropriate tension. Generally, some anchors may require a surgeon to tie a knot in the suture, or may be termed "knotless," i.e., no knot is required to secure the soft tissue to the bone because a suture is retained by the anchor and the bone. The process of passing a suture through a soft tissue and tying a knot is time consuming and difficult to undertake in the tight space encountered during endoscopic surgery, and sometimes during conventional open surgery.

Anchor systems implanted by drilling a hole in the bone are complicated to use in that they require using multiple tools that must be inserted into the incision during the procedure, such as a separate insertion tool and a separate drilling tool. Such complex drilling anchor systems result in increased procedure times and added possibility of surgeon error during the extended procedures and tool switching.

Those skilled in the art will appreciate that anchors generally experience a wide range of stresses during insertion into a bone. Although some prior art anchors have attempted to incorporate polymeric materials in their construction, these anchors have, in practice, generally provided inadequate insertion and holding strengths. As a consequence, known anchor bodies and known bone-engaging means have generally been made from high strength, biocompatible metals, and metal alloys.

As the use of prior art anchoring devices has become more widespread, it has been found that known anchors suffer from a number of limitations. For example, forming both the anchor body and the bone-engaging means out of biocompatible metals and metal alloys increases the cost of manufacturing. Also, in many medical applications, it is desirable to minimize the metal remaining in the patient's body after surgery. Such metal may cause X-ray artifacts and may migrate due to patient rejection.

Due to the disadvantages of metal implants, a large number of different biocompatible polymeric and bioabsorbable materials have recently been developed and become widely used in medical implantations. Such materials are: (i) relatively low in cost; (ii) fully compatible with conventional fabrication methods; and (iii) capable of being absorbed into the body of the patient after surgery. There are several prior art anchors which are made of such materials.

At present, however, available polymeric and bioabsorbable materials generally do not possess the requisite mechanical properties to allow pushing in and adequate retention of the anchor in the bone without pre-drilling a hole in the bone and providing the anchor with some metal components. Some prior art anchors overcome this problem by providing anchors made of polymeric and bioabsorbable materials that have a metal tip strong enough to allow for the screwing-in or pushing-in of the anchor into the bone. However, a major disadvantage of such anchors is that the metal tip remains into the patient's bone, which increases the chances of anchor rejection and migration due to the patient's body rejecting the metal tip.

To this end, a need exists for a suture anchor system which allows a suture anchor to be implanted into bone with a single tool. It is to such a suture anchor system that the inventive concept disclosed herein is directed.

BRIEF DESCRIPTION OF THE DRAWINGS

FIG. 1 is a side elevational view of an embodiment of a suture anchor system constructed in accordance with the inventive concepts disclosed herein.

FIG. 2A is a side elevational view of an exemplary embodiment of a suture anchor constructed in accordance with the inventive concepts disclosed herein.

FIG. 2B is a front elevational view of the suture anchor of FIG. 2A.

FIG. 8 is a side elevational view of the distal end of the suture anchor system of FIG. 1.

FIG. 9 is a side elevational view of a suture anchor system including the suture anchor drive of FIG. 7 and the suture anchor shown in FIGS. 3A-3B.

FIG. 11A is a perspective view of a portion of another embodiment of a suture anchor system constructed in accordance with the inventive concepts disclosed herein.

FIG. 11B a cross-sectional view of the suture anchor system of FIG. 11A.

FIG. 16 is a perspective view of an embodiment of a suture anchor according to inventive concepts disclosed herein.

FIG. 17 is a cross sectional view taken along line 17-17 of FIG. 16.

FIG. 18 is a partial, cross sectional view of a distal end of the suture anchor drive of FIG. 14.

FIG. 19 is a cross sectional view of the proximal end of the suture anchor drive of FIG. 14 shown in a retracted position.

FIG. 20 is a cross sectional view of a distal end of the suture anchor drive of FIG. 19 with the suture anchor of FIG. 16 positioned thereon.

FIG. 21A is a cross sectional view of the proximal end of the suture anchor drive of FIG. 14 shown in an advanced position.

FIG. 23 is a cross-sectional view of another embodiment of the suture anchor system according to the inventive concepts disclosed herein.

FIG. 24 is a cross-sectional view of a leading end of the suture anchor drive of FIG. 23.

DETAILED DESCRIPTION OF EXEMPLARY EMBODIMENTS

Figure 3A:
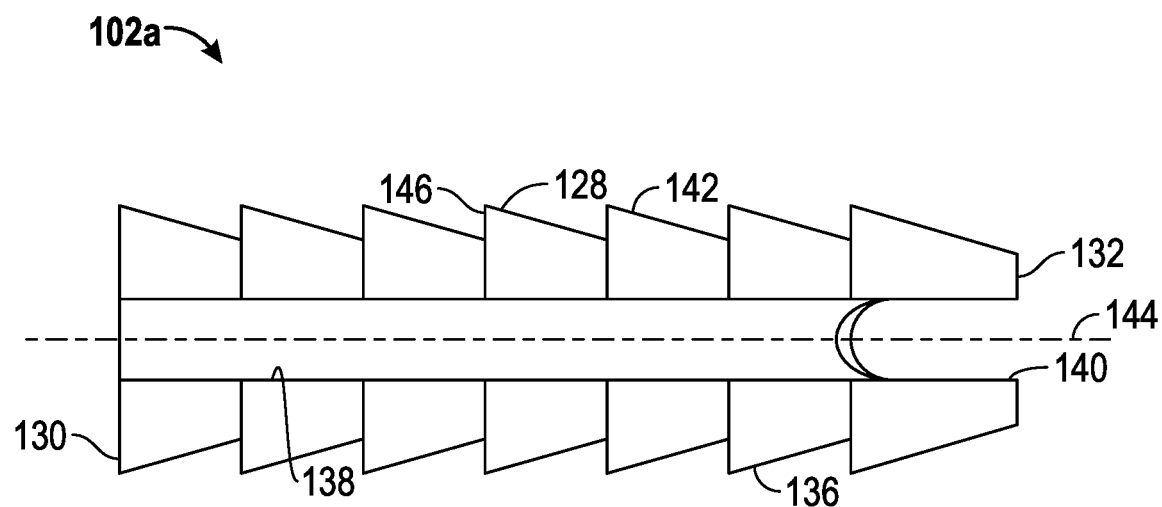
FIG. 3A is a side elevational view of another embodiment of a suture anchor constructed in accordance with the inventive concepts disclosed herein.

Before explaining at least one embodiment of the inventive concepts in detail, it is to be understood that the inventive concepts disclosed herein are not limited in their application to the details of construction, experiments, exemplary data, and the arrangement of the components set forth in the following description or illustrated in the drawings. The inventive concepts are capable of other embodiments or being practiced or carried out in various ways. Also, it is to be understood that the phraseology and terminology employed herein is for purposes of description and should not be regarded as limiting.

Referring now to the drawings, and more particularly to FIGS. 1-6, an exemplary embodiment of a suture anchor system 100 constructed in accordance with the inventive concepts disclosed herein. The suture anchor system 100 broadly comprises a suture anchor 102 and an anchor drive 104 for implanting the suture anchor 102 in bone.

As best shown in FIGS. 2A and 2B, the suture anchor 102 includes a body member 106 having a trailing end 108, a leading end 110, a cannula 112, a suture receiving notch 114, an alignment notch 116, and one or more retention ribs 118. The suture anchor 102 may be made of any suitable material or combinations of materials, e.g., a bioinert polymeric material such as polyetheretherketone (sold as PEEK™). The suture anchor 102 may also be made from a polymeric bioabsorbable material, such as polylactide-co-glycolide (PLGA), for example. The suture anchor 102 is made from a compressible resilient material such that the suture anchor 102 may be press-fitted inside a bone to ensure retention of the suture anchor 102 inside a bone even when there is no tension on the sutures. The suture anchor 102 may be made of various materials which may be uncoated, coated, or impregnated with various substances, such as, for example, antibiotics, titanium, APC, and combinations thereof.

The cannula 112 extends through the body member 106 from the trailing end 108 to the leading end 110. While the cannula 112 is shown as being cylindrical in shape, the cannula 112 may be implemented with other shapes, such as square, hexagonal, octagonal, pentagonal, star-shaped, oval, and triangular, for example. In some embodiments, the cannula 112 may have a rectangular, square, or other suitable shape, such that a correspondingly shaped rod limits or prevents rotation of the suture anchor 102 relative to the rod, as will be described below with reference to FIGS. 11A-11B.

The leading end 110 of the body member 106 may be tapered toward a longitudinal axis 120 to facilitate insertion of the suture anchor 102 into a bone. The suture anchor 102 is implanted into a bone with the leading end 110 first, to a depth such that the trailing end 108 is flush or such that the trailing end 108 sits just below the surface of the bone. In one embodiment, the suture anchor 102 is about 10 mm long, but other suitable sizes may be implemented as will be understood by persons of ordinary skill in the art. It is to be understood that body member 106 can have varying lengths and diameters according to the size of the implantation site, and the loads expected to be encountered by the sutures. As used herein, the term "suture" and any variations thereof is intended to include one or more sutures and suture loops.

The retention ribs 118 are shown as having two intersecting surfaces—a surface 122 which is tapered relative to the longitudinal axis 120 and a surface 124 which is perpendicular to the longitudinal axis 120. The surfaces 122 of the retention ribs 118 are adapted to allow the suture anchor 102 to be inserted into a bone, and the surfaces 124 retain the suture anchor 102 inside the bone by tensioning or press-fitting the retention ribs 118 against the bone. It is to be understood, however, that other conventional retention configurations may be used with the inventive concepts disclosed herein as will be apparent to a person of ordinary skill in the art presented with the instant disclosure. For example, there may be more than two surfaces 122 and 124, and such surfaces may be oriented in different angles relative to a longitudinal axis 120 or relative to one another. It is to be understood that other retaining means may be used with the inventive concepts disclosed herein, such as barbs, ridges, striations, and the like, and combinations thereof, for example.

The suture receiving notch 114 intersects the leading end 110 and is configured to receive one or more sutures therein. The suture receiving notch 114 may be wedge-shaped so as to taper in a proximal direction with a widest point at the leading end 110. Once the suture anchor 102 is inserted into a bone, a portion of a suture or a suture loop can be secured, at least in part, due to compression of opposing surfaces of the suture receiving notch 114 on the suture. The suture or suture loop may be further secured by a press-fit between the retention ribs 118 and a bone, such that a knot is not needed to secure the suture or suture loop, as will be described in more detail with reference to FIGS. 12A-12E below. As will be understood by persons of ordinary skill in the art, the tension of the suture may be adjusted prior to the insertion of suture anchor 102 into a patient's bone. The suture anchor 102 can be used with a suture-first technique, e.g., the suture has been attached to the soft tissue prior to anchor insertion.

The alignment notch 116 may cooperate with an implant alignment protrusion 126 of the anchor drive 104 (FIG. 8) which is adapted to mate with the alignment notch 116 to limit or prevent the rotation of the suture anchor 102 relative to the anchor drive 104. It is to be understood that while the alignment notch 116 is shown as substantially rectangular in shape, other shapes may be utilized to correspond to the shape of the implant alignment protrusion 126, such as triangular, square, circular, oval, and star-shaped, for example. It is to also be understood that more than one alignment notch 116 may be formed in the suture anchor 102. It is to be further understood that the implant alignment protrusion 126 may be formed as a groove or a protrusion on the rod 168 of the anchor drive 104. The suture anchor 102 may be formed by any conventional process, such as injection molding, press-molding, and combinations thereof, for example.

Figure 3B:
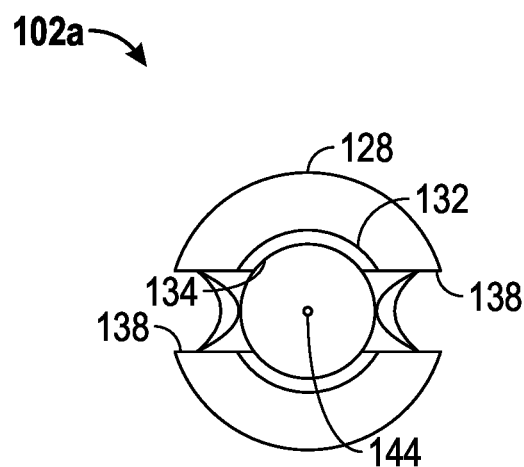
FIG. 3B is a front elevational view of the suture anchor of FIG. 3A.

Referring now to FIGS. 3A and 3B, shown therein is another embodiment of a suture anchor 102a. The suture anchor 102a is constructed similarly to the suture anchor 102. The suture anchor 102a has body member 128 which has a trailing end 130, a leading end 132, a cannula 134, one or more retention ribs 136, one or more suture channels 138, and a suture receiving notch 140.

The cannula 134 extends through the center of the body member 128 from the trailing end 130 to the leading end 132. The cannula 134 is shown as being cylindrical in shape, but it is to be understood that a cannula 134 according to the inventive concepts disclosed herein may be implemented with other shapes, such as square, hexagonal, octagonal, pentagonal, star-shaped, oval, and triangular, for example.

The retention ribs 136 are shown as having a surface 142 which is tapered relative to a longitudinal axis 144 and a surface 146 which is perpendicular to the longitudinal axis 144. It is to be understood, however, that other conventional retention configurations may be used with the inventive concepts disclosed herein. The surfaces 142 of the retention ribs 136 are configured to allow the suture anchor 102a to be inserted into a bone, and the surfaces 146 retain the suture anchor 102 inside the bone by tensioning or press-fitting the retention ribs 136 against the wall of the bone.

The suture channels 138 and the suture receiving notch 140 cooperate to allow one or more sutures to be threaded down into a first one of the suture channels 138, through the suture receiving notch 140, and up into a second suture channel 138. As will be understood by persons of ordinary skill in the art, even when the suture anchor 102a is inserted into a bone, the suture tension may be adjusted by a surgeon and secured by tying a knot. The suture anchor 102a may be made of similar materials and with similar methods as the suture anchor 102.

Figure 4A:
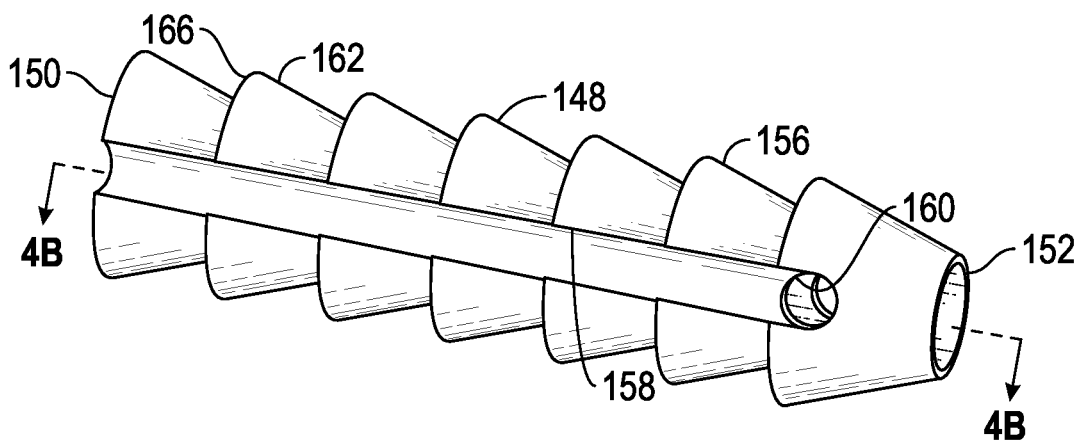
FIG. 4A is a side elevational view of another embodiment of a suture anchor constructed in accordance with the inventive concepts disclosed herein.
Figure 4B:
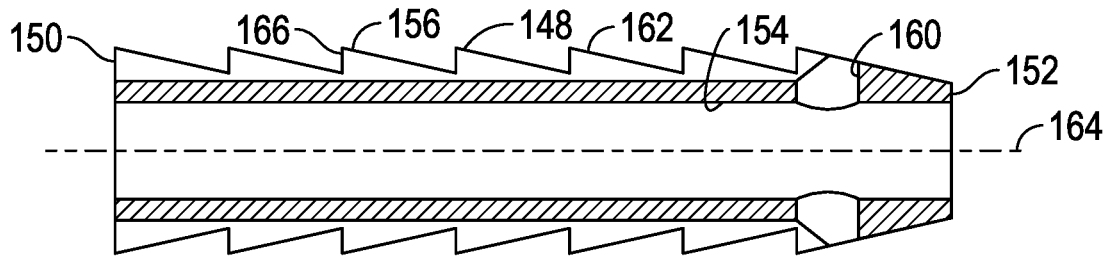
FIG. 4B is sectional view taken along line 4B-4B of FIG. 4A.

Referring now to FIGS. 4A and 4B, shown therein is another embodiment of a suture anchor 102b according to the inventive concepts disclosed herein. The suture anchor 102b is constructed similarly to suture anchors 102 and 102a. The suture anchor 102b has a body member 148 with a trailing end 150, a leading end 152, a cannula 154, one or more retention ribs 156, one or more suture channels 158, and one or more suture apertures 160.

The cannula 154 extends substantially through the center of body member 148 from the trailing end 150 to the leading end 152. The cannula 154 is shown as being cylindrical in shape, but it is to be understood that a cannula 154 according to the instant inventive concept may be implemented with other shapes, such as square, hexagonal, octagonal, pentagonal, star-shaped, oval, and triangular, for example.

The retention ribs 156 are shown as having a surface 162 which is tapered relative to a longitudinal axis 164 and a surface 166 which is perpendicular to the longitudinal axis 164. It is to be understood however that other conventional retention configurations may be used with the inventive concepts disclosed herein. The surfaces 162 of the retention ribs 156 are adapted to allow the suture anchor 102b to be inserted into a bone, and the surfaces 166 retain the suture anchor 102b inside the bone by tensioning or press-fitting the retention ribs 156 against the wall of the bone.

The suture channels 158 and the suture apertures 160 cooperate to allow one or more sutures to be threaded down into one of the suture channels 158, through the suture apertures 160, and up a second suture channel 158. As will be understood by a person or ordinary skill in the art, the suture tension may be adjusted by a surgeon and secured by tying a knot when the suture anchor 102b is inserted into a bone. The suture anchor 102b may be made of similar materials and with similar methods as the suture anchors 102 and 102a.

Figure 5:
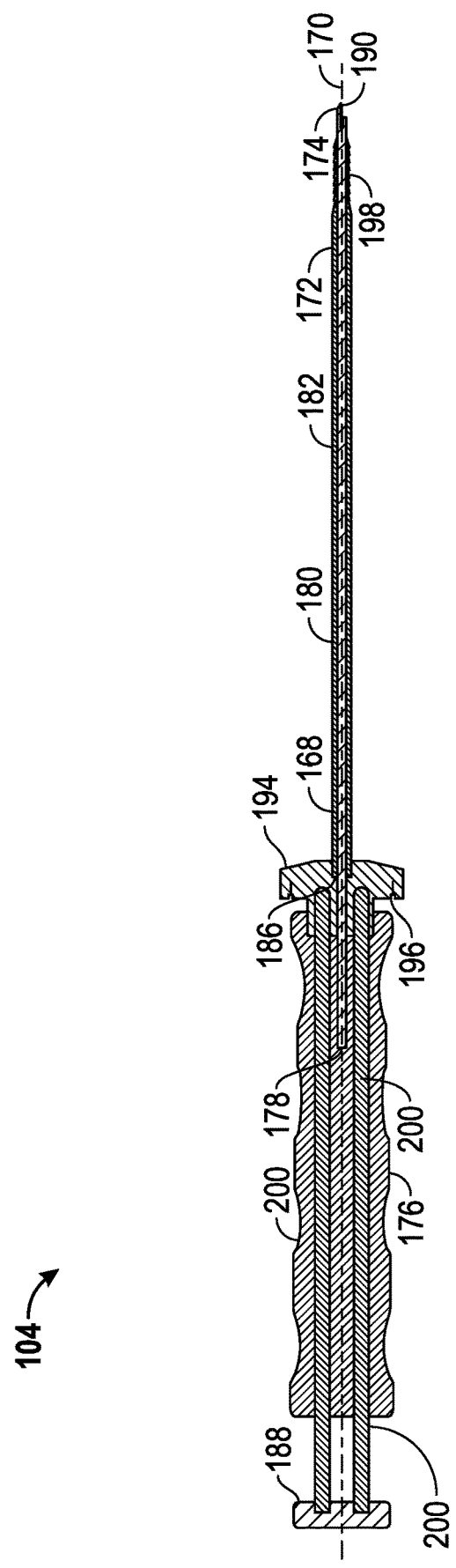
FIG. 5 is a cross-sectional view of an embodiment of the suture anchor system of FIG. 1.
Figure 6:
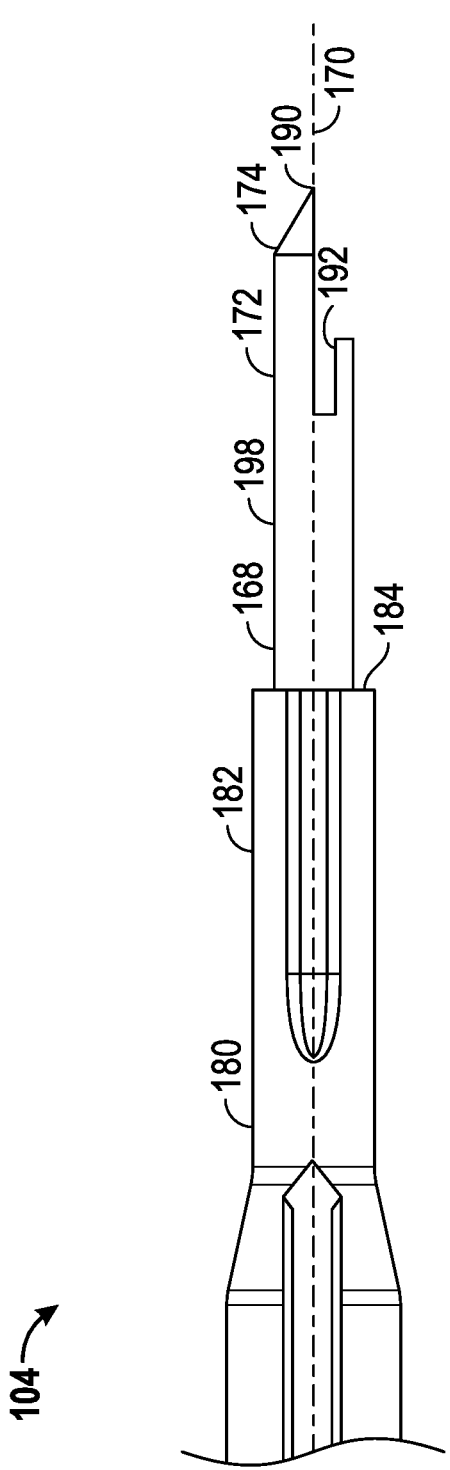
FIG. 6 is an enlarged side elevational view of a distal end of a suture anchor drive.
Figure 7:
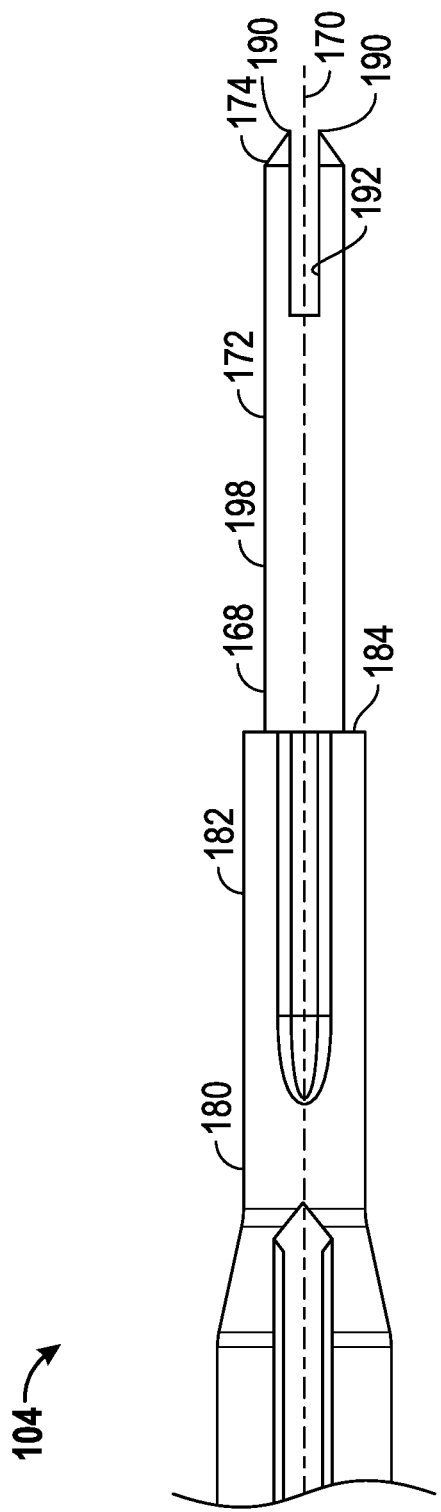
FIG. 7 is an enlarged side elevational view of a distal end of another embodiment of a suture anchor drive.

Referring now to FIGS. 5-7, the anchor drive 104 is illustrated in more detail. The anchor drive 104 includes a rod 168, a handle 176, and an impactor 180. The rod 168 has a longitudinal axis 170, an awl 172 formed on a leading end 174 and a trailing end 178. In one embodiment, the awl 172 includes a point 190 (FIG. 6) and at least one suture receiving notch 192. The awl 172 tapers to the point 190 configured to pierce a bone when force is applied to the rod 168. As shown in FIG. 6, the point 190 is oriented such that it is in alignment with the longitudinal axis 170 of the rod 168. Alternatively, as shown in FIG. 7, the awl 172 may include two points 190 symmetrically positioned along the longitudinal axis 170. The awl 172 may be made from a rigid metal such as stainless steel, titanium, or other suitable metals or alloys, for example. The suture receiving notch 192 is configured to receive and retain one or more surgical sutures or suture loops therein and insert such sutures or suture loops into the bone by the insertion of the awl 172.

The handle 176 is connected to the trailing end 178 of the rod 168 and may be any conventional surgical instrument handle 176. For example, the handle 176 may be designed with a non-slip surface and shaped to be securely grasped by a user's hand. The handle 176 may be constructed from a variety of materials such as metals and plastics, for example, and may be adapted to be reusable and sterilized.

The impactor 180 includes an impactor sleeve 182 slidably positioned about the rod 168 and an impactor head 188 connected to the impactor sleeve 182. The impactor sleeve 182 is slidably movable along the rod 168 between a retracted position (FIGS. 1, 5, and 11A-11B) wherein a front end 184 of the impactor sleeve 182 is spaced a distance from the leading end 174 of the rod 168 so as to define an anchor holding area 198, and an advanced position (FIGS. 6-10) wherein the front end 184 of the impactor sleeve 182 is moved toward the awl 172 to advance an anchor 102 positioned on the anchor holding area 198 along the rod 168 toward the awl 172. The anchor holding area 198 is sized to receive and hold a suture anchor 102 positioned thereon a distance from the awl 172 so that the awl 172 may be inserted into a bone a selected depth without interference from the suture anchor 102. The impactor sleeve 182 may include an implant alignment protrusion 126 extending into the anchor holding area 198 when the impactor sleeve 182 is in its retracted position.

The impactor head 188 is connected to a rear end 186 of the impactor sleeve 182 and is configured and dimensioned to be impinged on by surgical hammer strokes during insertion of the suture anchor 102 into a bone. In one embodiment, the impactor head 188 is connected to the impactor sleeve 182 with a plurality of rods 200 slidably disposed through the handle 176 and a suture fixation collar 194. The suture fixation collar 194 has one or more notches 196 formed therein (FIG. 5). The one or more notches 196 are adapted to receive and hold one or more sutures (not shown) therein. The suture fixation collar 194 may be made of any suitable material such as plastics and metals, for example. The impactor head 188 can be made of any suitable material such as stainless steel, titanium, resilient plastics, and combinations thereof, for example. The impactor head 188 may be manipulated to slidably move the impactor sleeve 182 about the rod 168, as will be described below.

Referring now to FIG. 8, shown therein is an enlarged view of an embodiment of the suture anchor system 100 illustrating the suture anchor 102 positioned on the rod 168 of the anchor drive 104 with the impactor sleeve 182 in the advanced position. The awl 172 of the rod 168 is shown extending though the cannula 112 of the suture anchor 102 and past the leading end 110. The trailing end 108 of the suture anchor 102 is shown abutting the front end 184 of the impactor sleeve 182. The implant alignment protrusion 126 is shown inserted into the alignment notch 116. The suture receiving notch 114 of the suture anchor 102 is aligned with the suture receiving notch 192 of the awl 172 to allow for the insertion of a suture as will be described with reference to FIGS. 12A-12E below. Such alignment is maintained throughout the insertion process to prevent snagging or twisting of the suture.

Referring now to FIG. 9, shown therein is an enlarged view of another embodiment of a suture anchor system 100a according to the inventive concepts disclosed herein. The suture anchor 102a is shown positioned on the rod 168 of the anchor drive 104 with the impactor sleeve 182 in the advanced position. The awl 172 of the rod 168 is shown as having two points 190, and extending all the way though the suture anchor 102a and past the leading end 132. The trailing end 130 of the suture anchor 102a is shown abutting the front end 184 of the impactor sleeve 182. The suture channel 138 is shown extending the length of the suture anchor 102a. An optional suture guide 202 is shown formed in the impactor sleeve 182 and aligned with the suture channel 138. The suture receiving notch 140 of the suture anchor 102a is aligned with the suture receiving notch 192 of the awl 172. The suture receiving notch 140, the suture receiving notch 192, the suture channels 138, and the suture guide 202 cooperate with the notches 196 of the suture fixation collar 194 to allow a user to adjust the tension on a suture and secure the suture with a knot as will be described with reference to FIGS. 12A-12E below.

Figure 10:
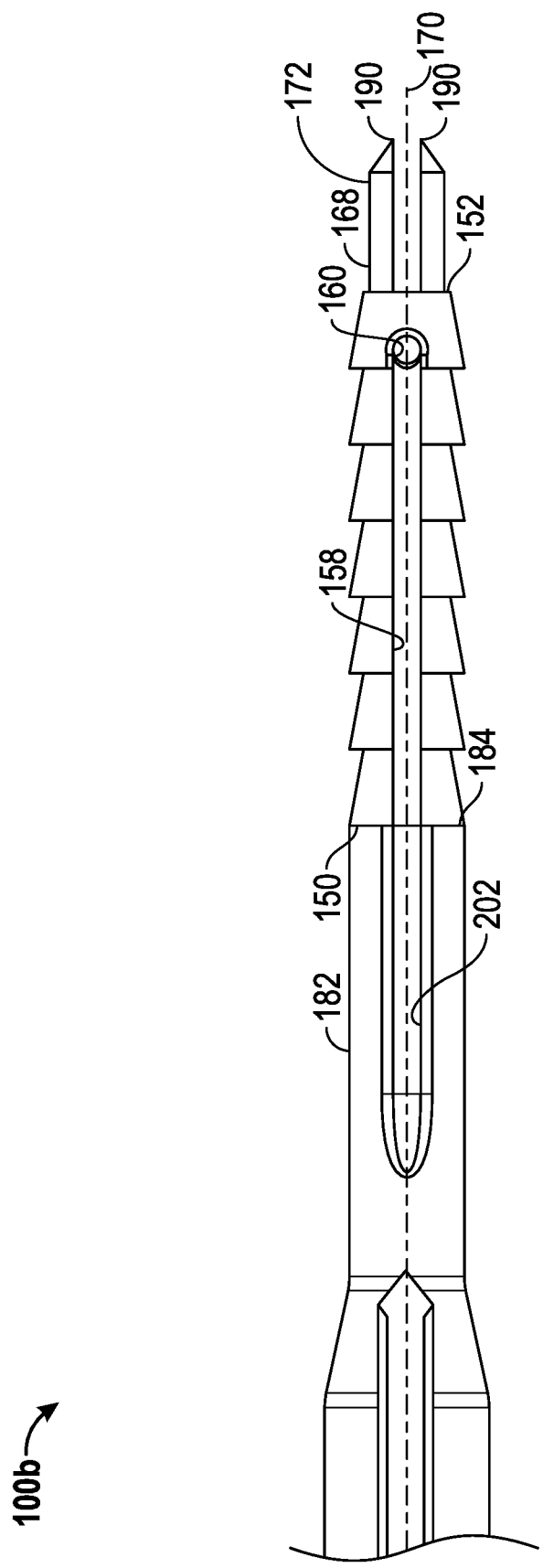
FIG. 10 is a side elevational view of an embodiment of a suture anchor system including the suture anchor drive of FIG. 7 and the suture anchor of FIGS. 4A and 4B.

Referring now to FIG. 10, shown therein is another embodiment of a suture anchor system 100b according to the inventive concepts disclosed herein. The suture anchor 102b is shown positioned on the rod 168 of the anchor drive 104 with the impactor sleeve 182 in the advanced position. The awl 172 of the rod 168 is shown as having two sharp points 190 and extending though the suture anchor 102b and past the leading end 152. The trailing end 150 of the suture anchor 102b is shown abutting the front end 184 of the impactor sleeve 182. A suture channel 158 is shown extending the length of the suture anchor 102b. An optional suture guide 202 is shown formed in the impactor sleeve 182 and aligned with the suture channel 158. The suture apertures 160 of the suture anchor 102b are aligned with the suture receiving notch 192 of the awl 172. The suture apertures 160, the suture receiving notch 192, the suture channels 158, and the suture guide 202 cooperate with the notches 196 of the suture fixation collar 194 to allow a user to adjust the tension on a suture and secure the suture with a knot as will be described with reference to FIG. 12A-12E below.

Referring now to FIGS. 11A and 11B, shown therein is yet another embodiment of a suture anchor system 100c according to the inventive concepts disclosed herein. The suture anchor 102 is shown positioned on a rod 168a of the anchor drive 104 with the impactor sleeve 182 positioned in the retracted position. The awl 172 of the rod 168a is shown extending though the cannula 112 of the suture anchor 102 and past the leading end 110. The trailing end 108 of the suture anchor 102 is shown abutting the front end 184 of the impactor sleeve 182. The rod 168a is shown as having a substantially hexagonal shape, and the cannula 112 is shown as having a corresponding hexagonal shape, such that when the suture anchor 102 is positioned onto the rod 168a, the suture receiving notch 114 of the suture anchor 102 is aligned with the suture receiving notch 192 of the awl 172 in order to allow for the insertion of a suture as will be described with reference to FIGS. 12A-12E below. In one embodiment, corresponding shapes of the rod 168a and the cannula 112 cooperate such that the cannula 112 is partially or completely prevented from rotating about the rod 168a when the suture anchor 102 is positioned on the rod 168a. Such alignment is maintained throughout the insertion process by the corresponding hexagonal shapes of the suture anchor 102 and the rod 168a, to prevent snagging and twisting of the suture. It is to be understood, however, that other suitable corresponding forms may be used for the suture anchor 102 and the rod 168a, provided that such corresponding forms are capable of partially or completely preventing rotation of the suture anchor 102 about the rod 168a. It is to be further understood that such complimentary shapes may also be used in combination with an alignment notch 116 and implant alignment protrusion 126 as described above with reference to FIG. 8.

In operation, an exemplary embodiment of a method for attaching a suture to a bone according to the inventive concepts disclosed herein may include attaching a suture to a soft tissue to be attached to a bone. The suture may be any conventional suture as will be understood by persons of ordinary skill in the art. The soft tissue may be a rotator cuff, a tendon, a ligament, a muscle, connective tissue, and combinations thereof, for example. The suture is attached to the soft tissue such that a suture loop is formed as will be appreciated by a person of ordinary skill in the art. Once the suture is attached to the soft tissue to be attached to a patient's bone, the suture anchor system 100 according to the inventive concepts disclosed herein may be used to anchor the suture to the patient's bone, by driving the awl 172 of the leading end 174 of the rod 168 into the bone.

FIGS. 12A-12E show an exemplary embodiment of a method for attaching soft tissue to a bone.

Figure 12A:
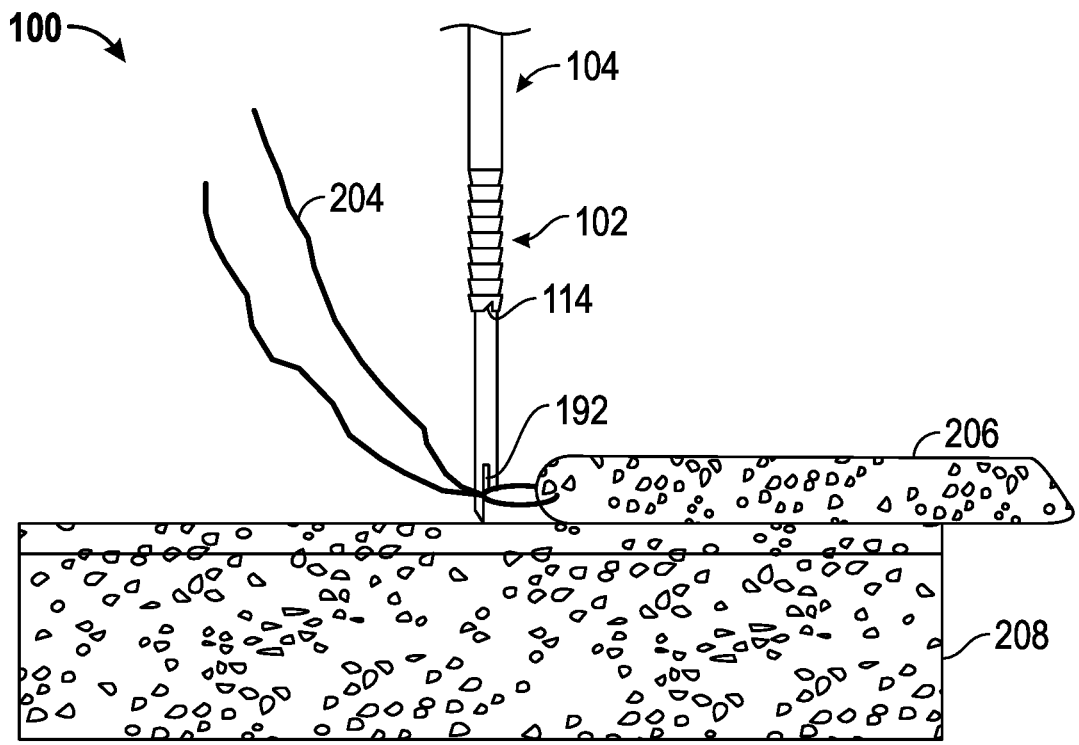
FIGS. 12A-12E are schematic diagrams illustrating steps of implanting a suture anchor into a bone.

Referring now to FIG. 12A, the suture anchor system 100 according to the inventive concepts disclosed herein is shown as having the anchor drive 104 and the suture anchor 102. A suture 204 attached to a soft tissue 206 is shown loaded into the suture receiving notch 192. The suture 204 will be used to anchor the soft tissue 206 into a bone 208. The suture anchor 102 is positioned on the anchor holding area 198 of the anchor drive 104 such that the suture receiving notch 114 is substantially aligned with the suture receiving notch 192 of the awl 172. This alignment may be maintained by matingly inserting the implant alignment protrusion 126 into the alignment notch 116. The suture 204 to be anchored may be loaded into the awl 172 of the anchor drive 104 such that the suture 204 is at least partially positioned within the suture receiving notch 114. An implantation location is identified and selected on the bone 208.

Figure 12B:
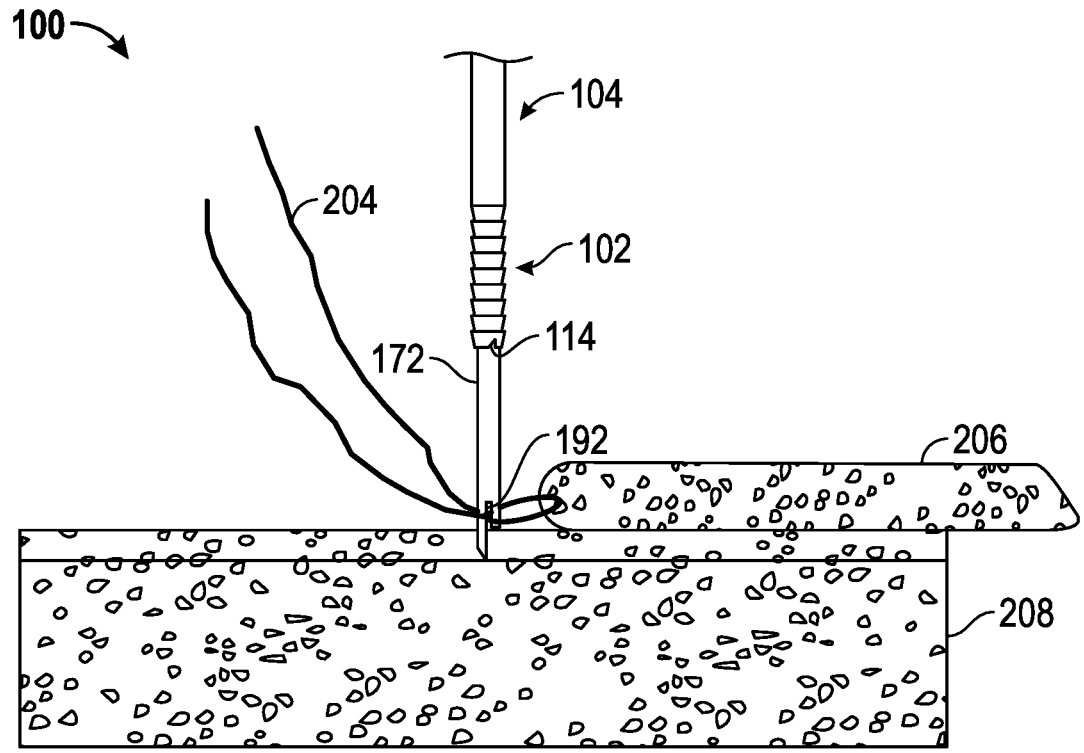

Referring now to FIG. 12B, once the implantation location is selected, the bone 208 is pierced with the awl 172 of the anchor drive 104. The force to pierce the bone 208 may be manually supplied by a surgeon pressing, rotating, and twisting the handle 176 of the rod 168 to drive the awl 172 into the bone 208, or by any other suitable means including impinging the anchor drive 104 with a hammer, for example.

Figure 12C:
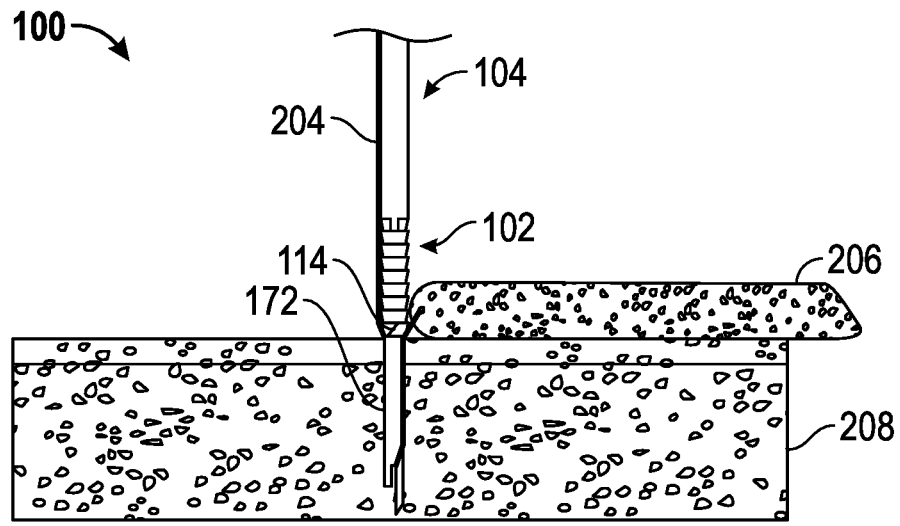

Referring now to FIG. 12C, the suture 204 is tensioned with the awl 172 inserted into the bone 208. The suture 204 is positioned relative to the suture anchor 102 such that an appropriate tension is created in the suture 204 to ensure proper attachment strength and location of the soft tissue 206 to the bone 208.

Figure 12D:
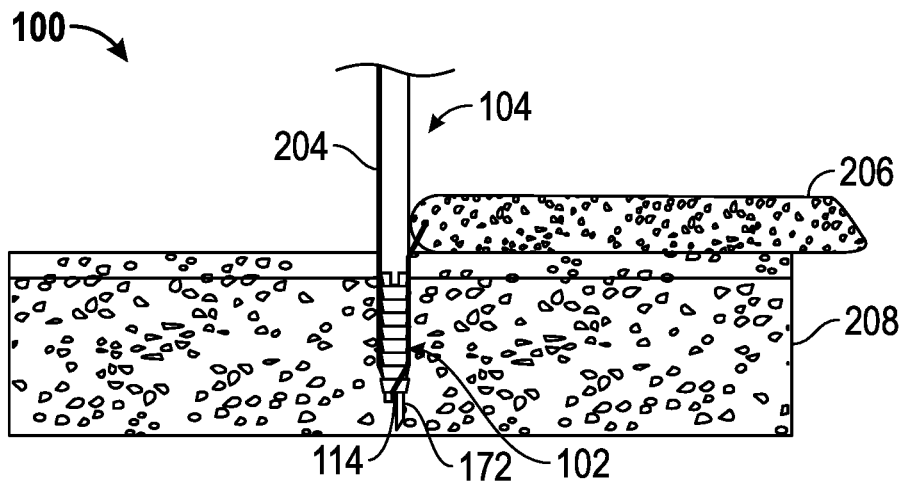

Next, as shown in FIG. 12D, the suture anchor 102 and the suture 204 are inserted into the bone 208 with the anchor drive 104 by manipulation of the impactor head 188, for example, by impinging the impactor head 188 with a surgical hammer, such that the impactor sleeve 182 moves over the anchor holding area 198 toward the advanced position so as to slide the suture anchor 102 from the anchor holding area 198 towards the leading end 174 of the rod 168. The front end 184 of the impactor sleeve 182 pushes against the trailing end 108 of the suture anchor 102 and the awl 172 of the rod 168 serves as a guide for the suture anchor 102. Optional markings (not shown) on the impactor sleeve 182 and the rod 168 may serve as a visual guide to indicate that the suture anchor 102 has been inserted to an appropriate depth.

Figure 12E:
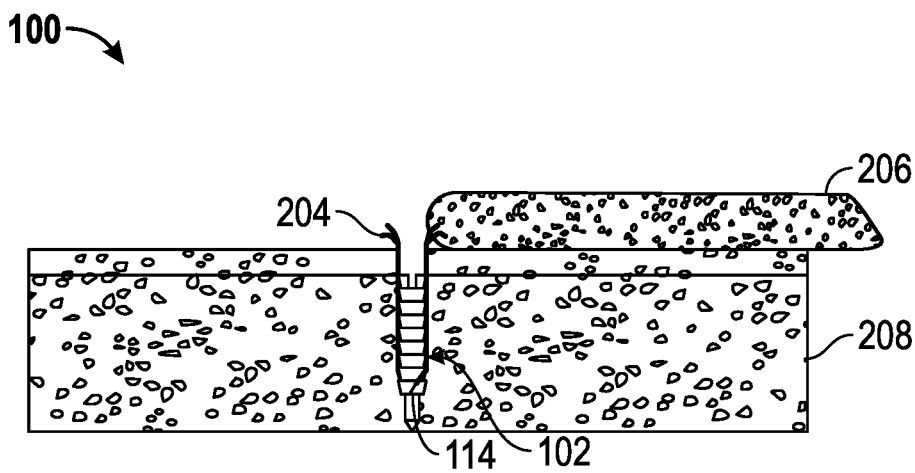
Figure 13:
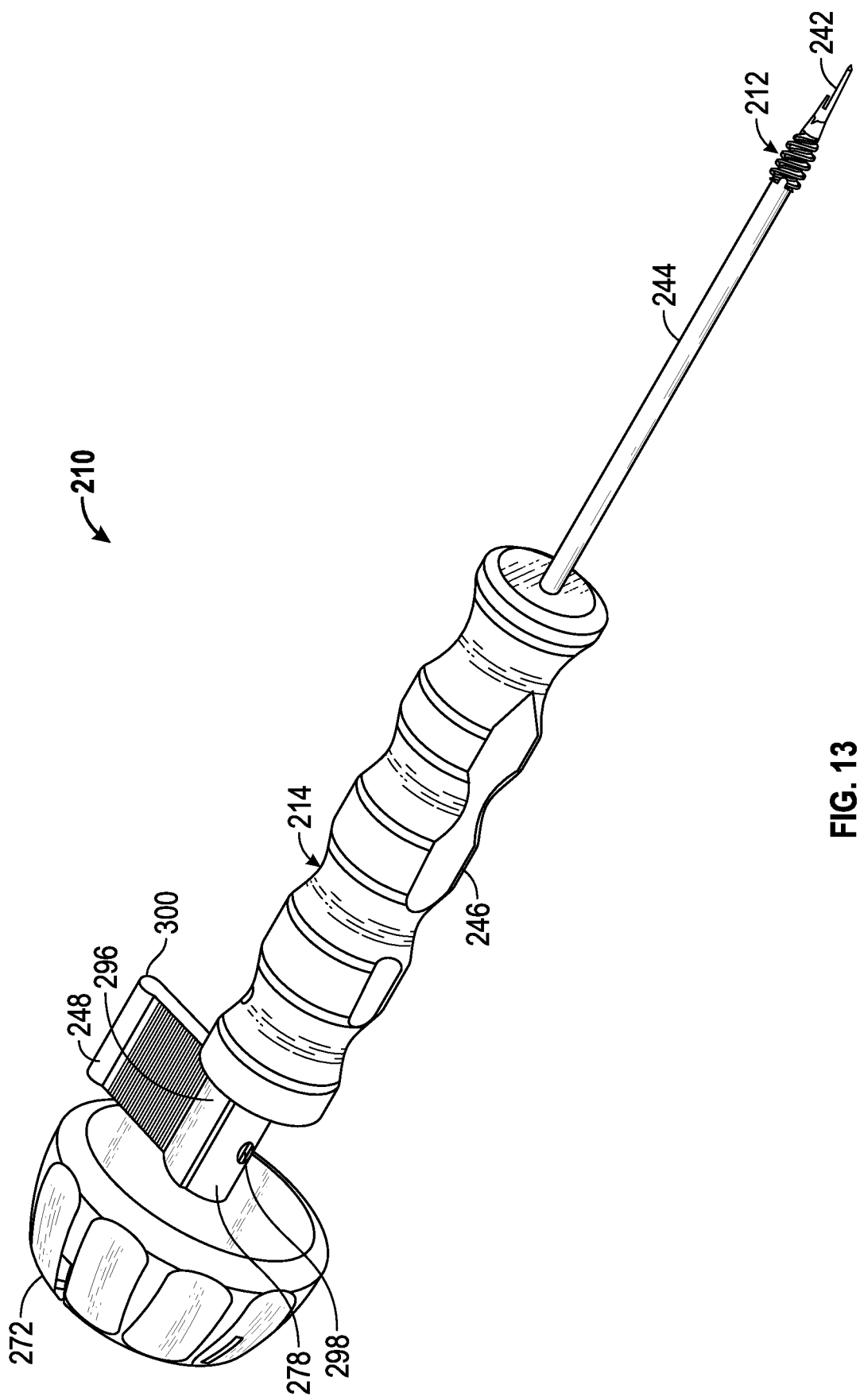
FIG. 13 is a perspective view of another embodiment of a suture anchor system according to the inventive concepts disclosed herein.
Figure 14:
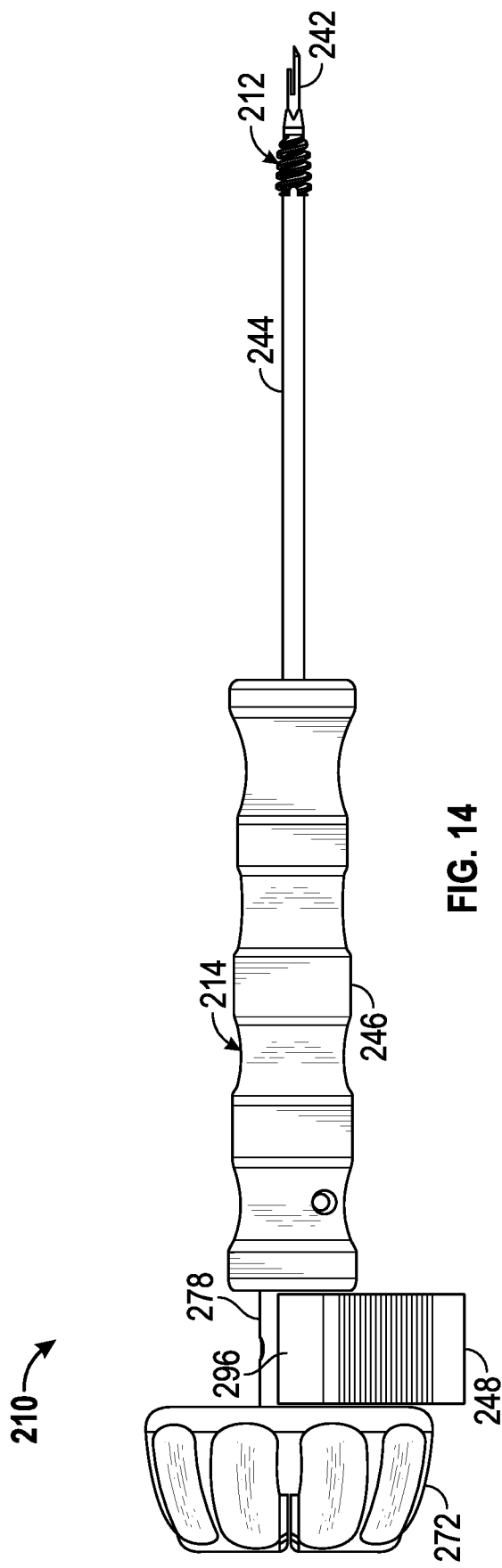
FIG. 14 is a side elevational view of the suture anchor system of FIG. 13.
Figure 15:
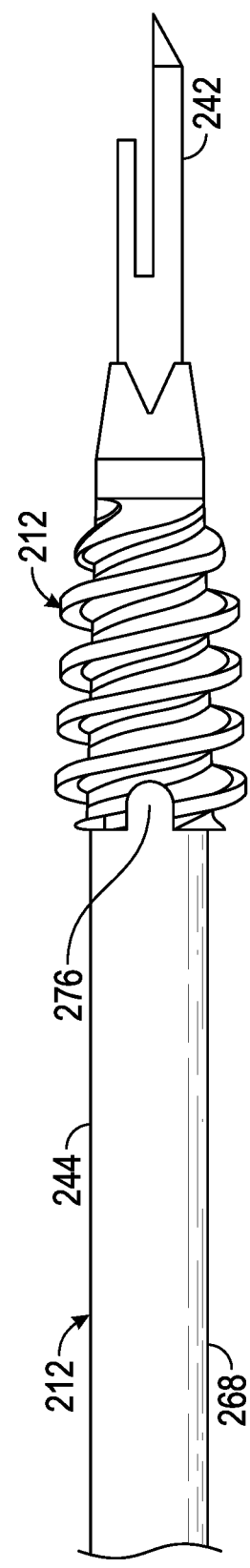
FIG. 15 is an enlarged side elevational view of a distal end of the suture anchor system of FIG. 14.
Figure 21B:
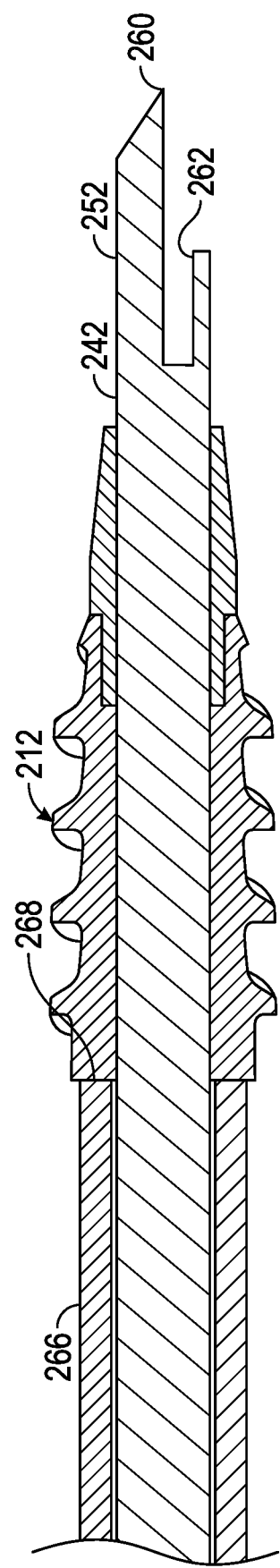
FIG. 21B is a partial cross sectional view of the distal end of the suture anchor drive of FIG. 14 shown in the advanced position.

As shown in FIG. 12E, the anchor drive 104 is removed, and the suture anchor 102 remains inside the bone 208 anchoring the soft tissue 206 to the bone 208. The anchor drive 104 may be removed from the bone 208 by withdrawing the awl 172 from the cannula 112 of the suture anchor 102 such that the rod 168 is detached from the suture anchor 102. The suture anchor 102 is retained in place by the compressive force between its retention ribs 118 and the walls of the bone 208. The suture 204 is likewise retained by the compressive force between the retention ribs 118 and the bone 208. Once the awl 172 has been removed, the suture receiving notch 114 of the suture anchor 102 is also retaining the suture 204 due to the compressive force exerted on the suture receiving notch 114 by the bone 208, which causes the wedge-shaped suture receiving notch 114 to act as a clip with respect to the suture 204. The ends of the suture 204 may be trimmed as necessary.

It will be understood that one, two, three, or more sutures 204, suture loops, and combinations thereof, may be attached to a bone 208 via a single or multiple suture anchors 102. For example, a particular suture 204 or suture loop may be attached to a bone 208 with two or more suture anchors 102 at two or more locations. As another example, several sutures 204 and suture loops may be attached at a location by a suture anchor 102. As yet another example, a single suture 204 may be attached to a bone 208 by a single suture anchor 102.

One or more sutures may be attached to bone using the suture anchor systems 100a and 100b in a similar manner to the method described in FIGS. 12A-12E above.

Referring now to FIGS. 13-21, another embodiment of a suture anchor system 210 constructed in accordance with the inventive concepts disclosed herein is illustrated. The suture anchor system 210 broadly comprises a suture anchor 212 and an anchor drive 214. The suture anchor 212 comprises a body member 216 and a tip member 218 rotatably connected to the body member 216. The body member 216 has a trailing end 220, a leading end 222, a cannula 224, an alignment notch 226, and a threaded outer surface 228.

The cannula 224 of the body member 216 is circular in shape and extends through the body member 216 from the trailing end 220 to the leading end 222. The cannula 224 is circular in shape to permit rotation of the body member 216 about the anchor drive 214 in a manner to be described below.

The alignment notch 226 is configured to receive a portion of the anchor drive 214 in a manner described below so that rotational force may be imparted to the body member 216 with the anchor drive 214. It is to be understood that while the alignment notch 226 is shown as substantially rectangular in shape, others shapes may be utilized to correspond to a portion of the anchor drive 214 as will be described below, such as triangular, square, circular, oval, and star-shaped, for example.

The threads formed on the threaded outer surface 228 may be any conventional threads, such as self-tapping threads, for example. The threads may be formed on the threaded outer surface 228 of the body member 216 by any conventional technique, such as cutting, molding, machining, and combinations thereof, for example. The threads formed on the threaded outer surface 228 are desirably atraumatic, i.e., the threads do not produce any additional or excessive tissue damage or injury as the suture anchor 212 is advanced or implanted into a bone.

The tip member 218 has a trailing end 230, a leading end 232, a suture receiving notch 234, and a cannula 236 extending therethrough. The tip member 218 tapers towards a longitudinal axis 238 to facilitate insertion of the suture anchor 212 into a bone. The suture receiving notch 234 intersects the leading end 232 and is configured to receive one or more surgical sutures therein. The suture receiving notch 234 may be substantially V-shaped, with one side being parallel to the longitudinal axis 238, and may taper in a proximal direction from the leading end 232. Once the suture anchor 212 is inserted into a bone, a portion of a suture 240 or a suture loop can be secured by the wedge shape of suture receiving notch 234 by being compressed, pinched, or clipped inside the suture receiving notch 234. The suture 240 or suture loop may be further secured by a press-fit between the suture anchor 212 and the bone, such that no knot is needed to secure the suture 204 or suture loop, as will be described below. As will be understood by persons of ordinary skill in the art, the tension of the suture 240 may be adjusted prior to insertion of the suture anchor 212 into a patient's bone. The suture anchor 212 can be used with a suture-first technique, e.g., the suture 240 has been attached to the soft tissue prior to suture anchor 212 insertion.

The tip member 218 is rotatably connected to the body member 216 in any suitable manner such as by press fitting the tip member 218 into the leading end 222 of body member 216 (i.e., a clip-on shoulder), for example. The tip member 218 and the body member 216 may also be attached to one another with the use of grooves or channels, for example.

The body member 216 and the tip member 218 of the suture anchor 212 may be made of any suitable material or combinations of materials, such as bioinert polymeric materials polyetheretherketone (sold as PEEK™), polylactide-co-glycolide (PLGA), for example. The suture anchor 212 may be uncoated, coated, or impregnated with various substances, such as for example antibiotics, titanium, APC, and combinations thereof. The suture anchor 212 may be made using any conventional methods, such as injection molding, casting, machining, molding, thermoplastic setting, and combinations thereof, for example.

Referring now to FIGS. 13-15 and 18-21, the anchor drive 214 comprises a rod 242, an impactor 244 movable about and along the rod 242, a handle 246 through which the rod 242 and the impactor 244 are disposed, and a spacer 248 for retaining the rod 242 and the impactor 244 in a fixed relationship relative to one another.

The rod 242 has a longitudinal axis 250, an awl 252 (FIG. 18) formed on a leading end 254, and a rod anchor 256 (FIG. 19) provided on a trailing end 258. In one embodiment, the awl 252 includes a point 260 and one or more suture holding notches 262. The awl 252 may taper to the one sharp point 260 configured to pierce a bone when force is applied to the rod 242. As shown in FIG. 18, the point 260 may be oriented such that it is in alignment with the longitudinal axis 250 of the rod 242. Alternatively, the awl 252 may include two or more sharp points symmetrically positioned along the longitudinal axis 250. The awl 252 may be made from a rigid metal such as stainless steel, titanium, or other suitable metals or alloys, for example. The suture holding notch 262 may be adapted to receive and retain one or more surgical suture 240 or suture loop therein and insert such one or more suture 240 or suture loop into the bone by the insertion of the awl 252.

The rod anchor 256 is connected to, or formed on the trailing end 258 of, the rod 242. The rod anchor 256 is generally cylindrically shaped and has a diameter greater than the diameter of the rod 242. The rod anchor 256 is provided with at least one transverse pin receiving opening 264.

The impactor 244 includes an impactor sleeve 266 rotatably and slidably positioned about the rod 242 and having a front end 268 (FIG. 18) and a rear end 270 (FIG. 19). To facilitate rotation of the impactor sleeve 266, an impactor head 272 is connected to the rear end 270 of the impactor sleeve 266. The impactor sleeve 266 is rotatably and slidably movable along the rod 242 between a retracted position (FIGS. 19 and 20) wherein the front end 268 of the impactor sleeve 266 is spaced a distance from the leading end of the rod 242 so as to define an anchor holding area 274, and an advanced position (FIGS. 21A and 21B) wherein the front end 268 of the impactor sleeve 266 is moved toward the awl 252 to advance the suture anchor 212 positioned on the anchor holding area 274 along the rod 242 toward the awl 252. The anchor holding area 274 is adapted to receive and hold the suture anchor 212 positioned thereon a distance from the awl 252 so that the awl 252 and sutures 240 being held by the suture holding notch 262 may be inserted into a bone a selected depth without interference from the suture anchor 212. The impactor sleeve 266 includes a drive protrusion 276 (FIG. 15) extending from the front end 268 of the impactor sleeve 266 that is matable with the alignment notch 226 of the suture anchor 212 so as to permit a rotational force to be imparted to the suture anchor 212 by the impactor sleeve 266.

The impactor head 272 is connected to the rear end 270 of the impactor sleeve 266 and is configured and dimensioned to be impinged on by surgical hammer strokes and to be manually rotated during insertion of the suture anchor 212 into a bone. In one embodiment, the impactor head 272 is connected to the impactor sleeve 266 with a connector 278 that defines a neck. The connector 278 is cylindrical in shape and has one end connected to the impactor head 272 and another end connected to the impactor sleeve 266 in such a way that rotation of the impactor head 272 causes the impactor sleeve 266 to rotate. The connector 278 has a recess 280 for slidably receiving the rod anchor 256. The recess 280 (FIG. 21A) of the connector 278 corresponds with a cannula 282 of the impactor head 272 so that the impactor sleeve 266 is slidably movable relative to the rod 242 and the rod anchor 256 between the retracted position and the advanced position. The connector 278 further has one or more transverse pin receiving openings 284 alignable with the pin receiving opening 264 of the rod anchor 256 when the impactor 244 is in the retracted position.

The impactor sleeve 266, the impactor head 272, and the connector 278 can be made of any suitable material such as stainless steel, titanium, plastics, and combinations thereof, for example. Also, while the impactor sleeve 266, the impactor head 272, and the connector 278 have been illustrated as being separate pieces, it will be appreciated that the impactor 244 may be formed as a single piece.

The handle 246 has a body member that has a central bore 286 for rotatably receiving the impactor sleeve 266 and a counterbore 288 for rotatably receiving a portion of the connector 278 such that the impactor 244 is rotatable relative to the handle 246 while being fixed in a longitudinal relationship. To this end, by way of example, the handle 246 may include a bearing assembly 290 to connect the connector 278 to the handle 246.

The handle 246 may be designed with a non-slip surface and shaped to be securely grasped by a user's hand. The handle 246 may be constructed from a variety of materials such as metals and plastics, for example. The handle 246 may further have a suture fixation collar 292. The suture fixation collar 292 has one or more suture retaining notch 294 formed therein (FIG. 19). The one or more suture retaining notch 294 is adapted to receive and hold one or more surgical sutures (not shown) therein.

The spacer 248 functions to maintain the rod 242 and the impactor 244 stationary relative to one another as the awl 252 is being inserted into a bone. The spacer 248 is removed to allow the impactor 244 to be rotated about the rod 242 and the rod anchor 256 and slide longitudinally relative to one another. The spacer 248 comprises a collar 296, a pin 298, and a tab 300. The spacer 248 can be constructed of any suitable material, such as titanium, stainless steel, plastics, polymers, resins, non-metals, and combinations thereof, for example.

The collar 296 is adapted to selectively grasp the connector 278 such that the spacer 248 can be removably attached to the connector 278. The collar 296 is configured to disengage the spacer 248 from the connector 278 when a predetermined amount of force is applied to the tab 300, for example. It is to be understood that while the collar 296 is shown as a semi-circular structure, some embodiments of the inventive concepts disclosed herein may comprise a spring-loaded collar 296, for example. It is to be further understood that the collar 296 may be omitted in some exemplary embodiments of the inventive concepts disclosed herein.

The pin 298 is shown to be cylindrically shaped and adapted to be removably inserted through one or more of the pin receiving openings 284 of the connector 278, and through the pin receiving opening 264 of the rod anchor 256.

The tab 300 is configured and sized to allow a user to position the spacer 248 about the connector 278 such that the collar 296 is disposed between the impactor head 272 and the handle 246 when the pin 298 is inserted through the pin receiving opening 284 of the connector 278 and through the pin receiving opening 264 of the rod anchor 256.

To attach the spacer 248 to the connector 278, the rod anchor 256 is seated in the recess 280 of the connector 278 and rotated as needed to align the pin receiving openings 264 and 284 of the rod anchor 256 and the connector 278, respectively. Next, the pin 298 is inserted through the aligned pin receiving openings 284 and the pin receiving opening 264 and the collar 296 is engaged with the connector 278.

In use, the suture anchor system 210 may be used to attach a soft tissue 302 to a bone 304 with one or more sutures, such as suture 240. The suture 240 may be any conventional suture 240 as will be understood by persons of ordinary skill in the art. The soft tissue 302 may be a rotator cuff, a tendon, a ligament, a muscle, connective tissue, and combinations thereof, for example. The suture 240 may be attached to the soft tissue 302 such that a suture loop is formed, as will be appreciated by a person of ordinary skill in the art. Once the suture 240 is attached to the soft tissue 302 to be attached to a patient's bone 304, the suture anchor system 210 according to the instant disclosure may be used to anchor the suture 240 to the patient's bone 304.

One exemplary embodiment of a method for attaching a soft tissue 302 to a bone 304 generally proceeds as described in FIGS. 22A-22E. A suture anchor 212 may be positioned on the anchor holding area 274 of the anchor drive 214 such that the suture receiving notch 234 is substantially aligned with the suture holding notch 262 of the awl 252. The suture 240 to be anchored is loaded into the suture holding notch 262 such that the suture 240 is at least partially positioned within the suture holding notch 262.

Figure 22A:
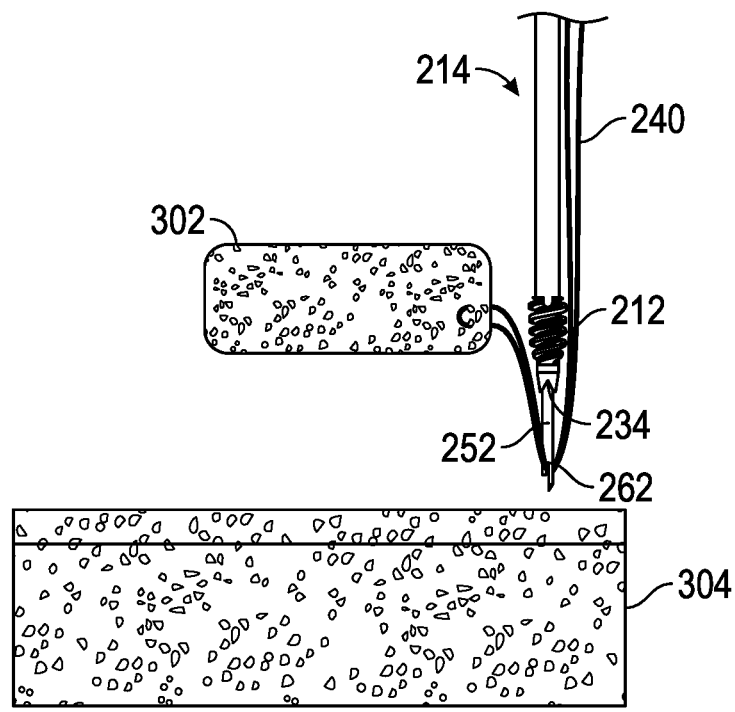
FIGS. 22A-22E are schematic diagrams illustrating steps of implanting the suture anchor of FIG. 16 into a bone.
Figure 22B:
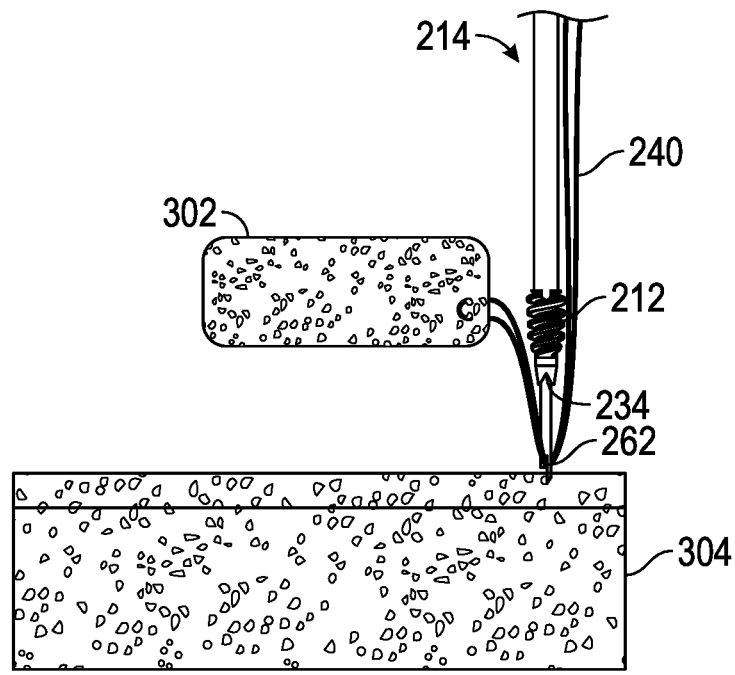
Figure 22C:
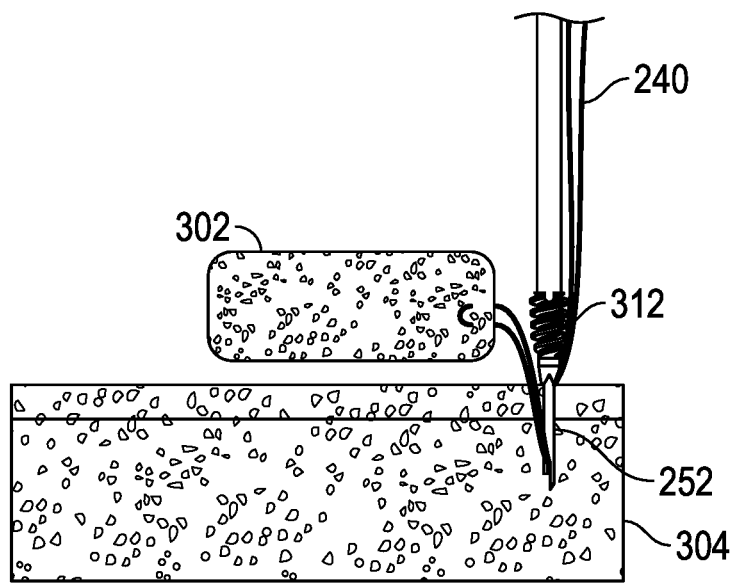

An implantation site is identified and selected on a patient's bone 304 (FIG. 22B). The bone 304 is pierced (FIG. 22C) at the location by advancing the awl 252 into the bone 304. The force to pierce the bone 304 may be manually supplied by a surgeon pressing the handle 246 and/or the impactor head 272 to advance the awl 252 into the bone 304 or by any other suitable means including impinging the impactor head 272 of the anchor drive 214 with a surgical hammer, for example. As illustrated in FIG. 22C, the suture 240 is advanced into the bone 304 along with the awl 252. The suture 240 is maintained under tension (e.g., by securing the suture 240 into the suture retaining notch 294), such that the suture 240 is prevented from rotating or twisting as the awl 252 is advanced into the bone 304. The suture 240 is tensioned relative to the anchor drive 214 such that an appropriate tension is created in the suture 240 to ensure proper attachment strength and location of the soft tissue 302 to the bone 304. In addition, the tip member 218 of the suture anchor 212 is advanced into the bone 304 with the anchor drive 214 such that the tip member 218 is inserted into the bone 304.

The spacer 248 is removed from the impactor 244, such as by applying a predetermined amount of force to the tab 300 to disengage the collar 296 from the connector 278, and removing the pin 298 from the pin receiving openings 284 and from the transverse pin receiving opening 264. The spacer 248 may be disposed of or sterilized and reused. As will be understood by persons of ordinary skill in the art, removing the spacer 248 allows the rod anchor 256 to rotate and slide relative to the connector 278. This, in turn, allows the impactor sleeve 266 to rotate and slide relative to the rod 242. The rod anchor 256 may be received by the cannula 282 of the impactor head 272 during this step, as shown in FIG. 21A.

Figure 22D:
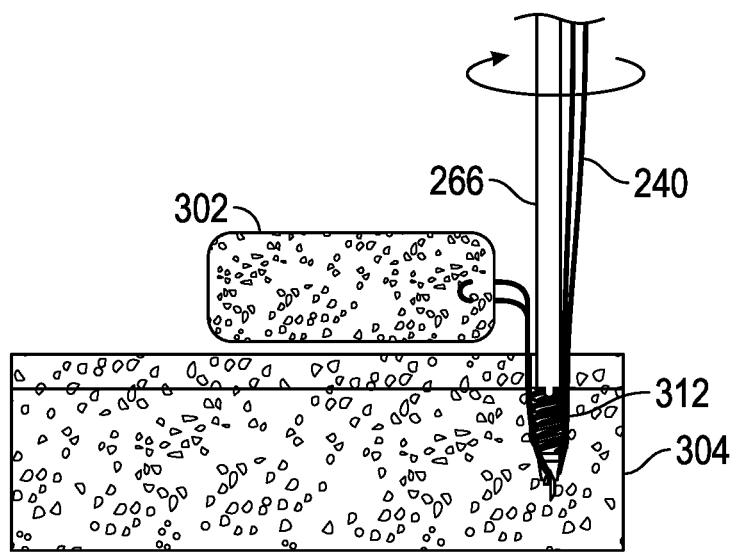

As illustrated in FIG. 22D, rotational force is applied to the impactor head 272 so as to cause the impactor sleeve 266 to rotate the body member 216 and cause the threaded outer surface 228 to engage the bone 304 and cause the suture anchor 212 to begin advancing into the bone 304. Optional marking(s) (not shown) on the impactor sleeve 266 may serve as a visual guide to indicate that the suture anchor 212 has been advanced into the bone 304 to desired depth.

As will be understood by persons of ordinary skill in the art, the compressive forces exerted on the tip member 218 by the bone 304, prevent the tip member 218 from rotating as the body member 216 is rotated and advanced into the bone 304 such that the alignment between the suture receiving notch 234 and the suture holding notch 262 is substantially maintained as the suture anchor 212 is implanted into the bone 304. The impactor sleeve 266 is rotated until the suture anchor 212 is advanced into the bone 304 to a desired depth.

Figure 22E:
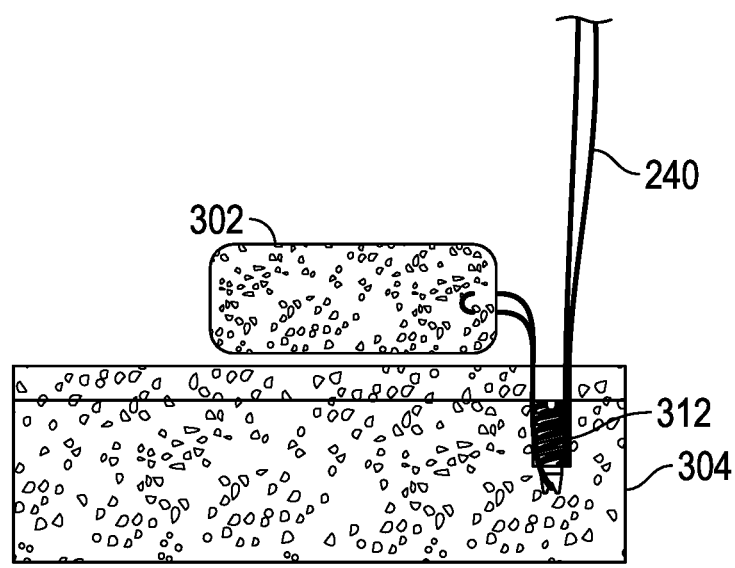

As illustrated in FIG. 22E, the anchor drive 214 may be removed from the bone 304 by withdrawing the awl 252 from the bone 304 such that the suture anchor 212 slides off the rod 242. The ends of the suture 240 may be trimmed as necessary or desired. It will be understood that one, two, three, or more sutures 240, suture loops, and combinations thereof, may be attached to a bone 304 via a single or multiple suture anchors 212. For example, a particular suture 240 may be attached to a bone 304 with two or more suture anchors 212 at two or more locations. As another example, several sutures 240 may be attached at a location by the suture anchor 212. As yet another example, a single suture 240 may be attached to a bone 304 by a single suture anchor 212.

Referring now to FIGS. 23 and 24, another embodiment of a suture anchor system 310 constructed in accordance with the inventive concepts disclosed herein is illustrated. The suture anchor system 310 has a suture anchor 312 and an anchor drive 314.

The suture anchor 312 includes a body member 316 having a trailing end 318, a leading end 320, a cannula 322, a suture receiving notch 324, an alignment notch (not shown), and one or more retention ribs 326. The suture anchor 312 may be constructed or implemented similarly to the suture anchor 102, for example. In some embodiments, the suture anchor 312 may be constructed or implemented similarly to the suture anchor 102a, the suture anchor 102b, the suture anchor 102c, or the suture anchor 212 described above, for example. The cannula 322 extends through the body member 316 from the trailing end 318 to the leading end 320.

The anchor drive 314 has a rod 328, a handle 336, and an impactor 340. The rod 328 is includes a longitudinal axis 330, an awl 332 formed on a leading end 334, and a trailing end 338. The anchor drive 314 is similar to the anchor drive 104 described above, except that the anchor drive 314 is cannulated to enable a suture loop to be formed adjacent the leading end 334 of the rod 328 in a manner to be discussed below. In one embodiment, the rod 328 is provided with a cannula 350 extending from the leading end 334 to the trailing end 338. The cannula 350 is aligned with a cannula 351 of the handle to form a cannula extending from the leading end 334 of the rod to the proximal end of the handle 336.

The cannula 350 opens at the end 354 such that a suture loop 352 may extend past the end 354, or past the projection 356 (in which case the suture loop 352 would also extend past the end 354 as will be appreciated by persons of ordinary skill in the art). The suture loop 352 is adapted to capture one or more sutures.

A cannula access opening 362 is shown positioned on an end 364 of the handle 336 and the cannula 350 which extends substantially through the end 364 of the handle 336 opens into the cannula access opening. The cannula access opening 362 is shown as being substantially coaxial with the cannula 350, but it is to be understood that the cannula access opening 362 may by angled relative to the cannula 350 at an angle varying from about 0 to about 90 degrees, for example. The cannula access opening 362 is adapted to allow a surgeon to thread the suture loop 352 through the cannula 350, and to adjust the tension and position of the suture loop 352 as desired, for example. The suture loop 352 may be formed by folding a surgical suture and inserting it into the cannula 350 such that the suture loop 352 extends past the end 354 or past the projection 356, for example. The suture loop may likewise be formed by threading one end of a suture through the cannula access opening 362, all the way through the cannula 350 and past the end 354 or the projection 356, and then doubling back through the cannula 350 and out the cannula access opening 362 to leave the suture loop 352 extending past the end 354 or past the projection 356, for example.

Figure 25A:
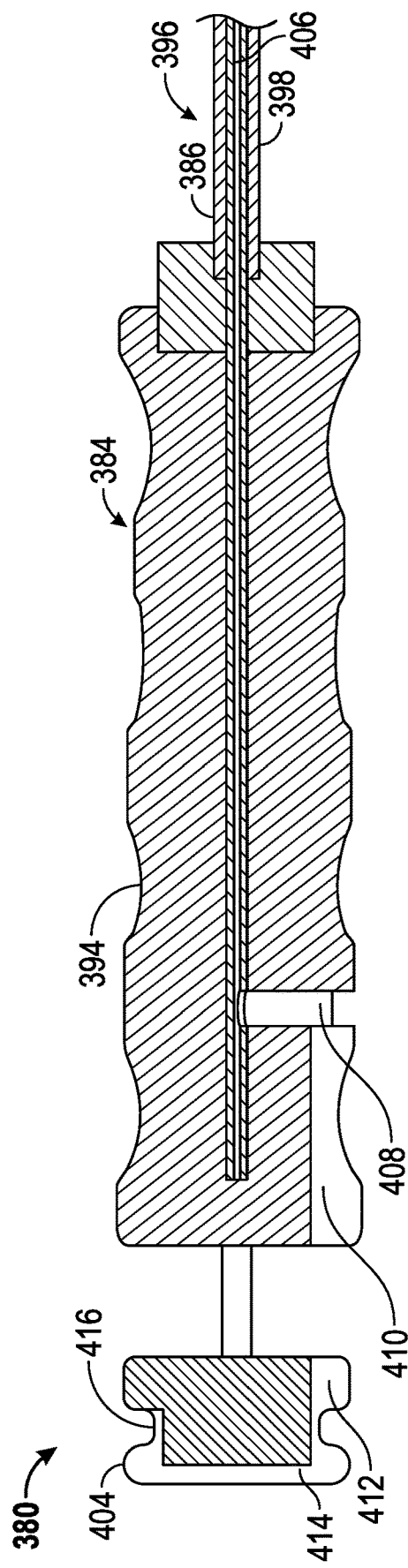
FIG. 25A is a cross-sectional view of another embodiment of a suture anchor system according to the inventive concepts disclosed herein.
Figure 25B:
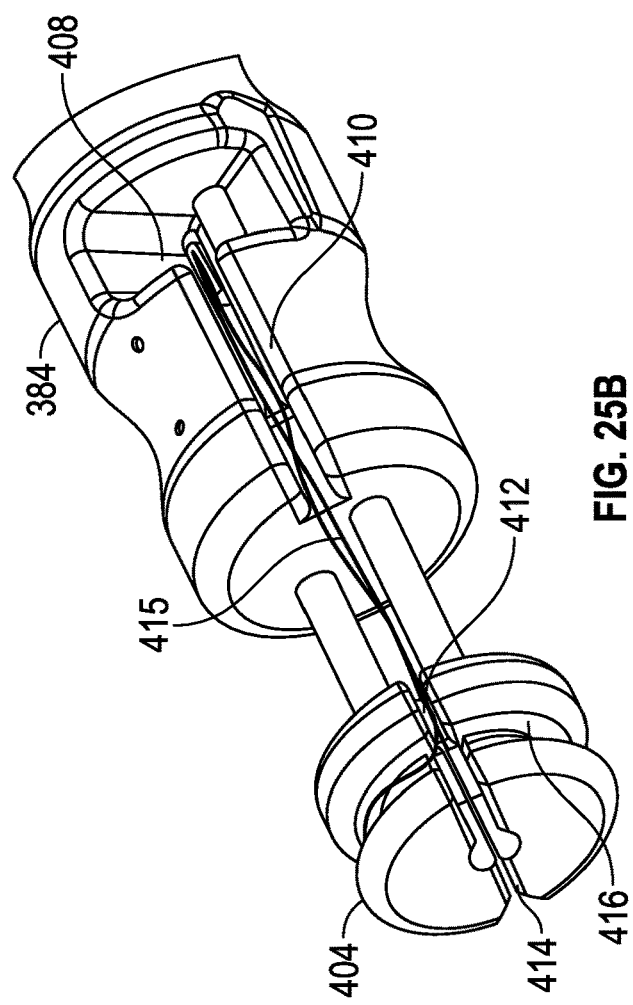
FIG. 25B is a perspective view of a trailing end of the suture anchor system shown in FIG. 25A.

Referring now to FIGS. 25A-25B, shown therein is an exemplary embodiment of another suture anchor system 380. The suture anchor system 380 is similar in construction and function to the suture anchor system 310 described above. The suture anchor system 380 is shown to include a suture anchor 312 and an anchor drive 384. The anchor drive 384 is similar in construction and function to the anchor drive 314 except the anchor drive 384 is constructed to provide lateral access to the cannula. More specifically, the anchor drive 384 has a rod 386 with a longitudinal axis 388, an awl 390 formed on a leading end 392; a handle 394 provided on a trailing end 392 of the rod 386; and an impactor 396 having an impactor sleeve 398 slidably positioned about the rod 386 and having a front end 400 and a rear end 402 and an impactor head 404 connected to the rear end 402 of the impactor sleeve 398. In one embodiment, the rod 386 is provided with a cannula 406 extending from the leading end 392 to the trailing end 394. The handle 384 is provided with a cannula access opening 408 in a side of the handle 384 such that one or more suture loop 352 may be inserted or threaded into the cannula 406 via the cannula access opening 408. The cannula access opening 408 is shown as being substantially perpendicular to the cannula 406, but it is to be understood that the cannula access opening 408 may be angled relative to the cannula.

As best shown in FIG. 25B, the handle 384 has a suture receiving slot 410 extending longitudinally from the cannula access opening 408 to proximal end of the handle 384. Similarly, the impactor head 404 is provided with a suture receiving slot 412 extending longitudinally along the impactor head 404 in alignment with the suture receiving slot 410 of the handle 384. The impactor head 404 may be further provided with a lateral suture receiving slot 414 extending laterally across the impactor head 404 in communication with the suture receiving slot 410. Further, the impactor head 404 may be configured like a spool where the impactor head 404 has an annular groove 416.

The suture receiving slot 410, the suture receiving slot 412, the lateral suture receiving slot 414 and the annular groove 416 may be employed to receive and retain the one or more suture forming the one or more suture loop therein such that the one or more sutures forming the one or more suture loop 352 may be securely threaded or spooled about the impactor head 404 during the surgical procedure as will be described below. Any excess suture may be spooled around the impactor head 404 after the implantation of the suture anchor 312, for example.

Referring now to FIGS. 26A-26E, shown therein is an exemplary method of using a suture anchor system 310 according to the inventive concepts disclosed herein.

Figure 26A:
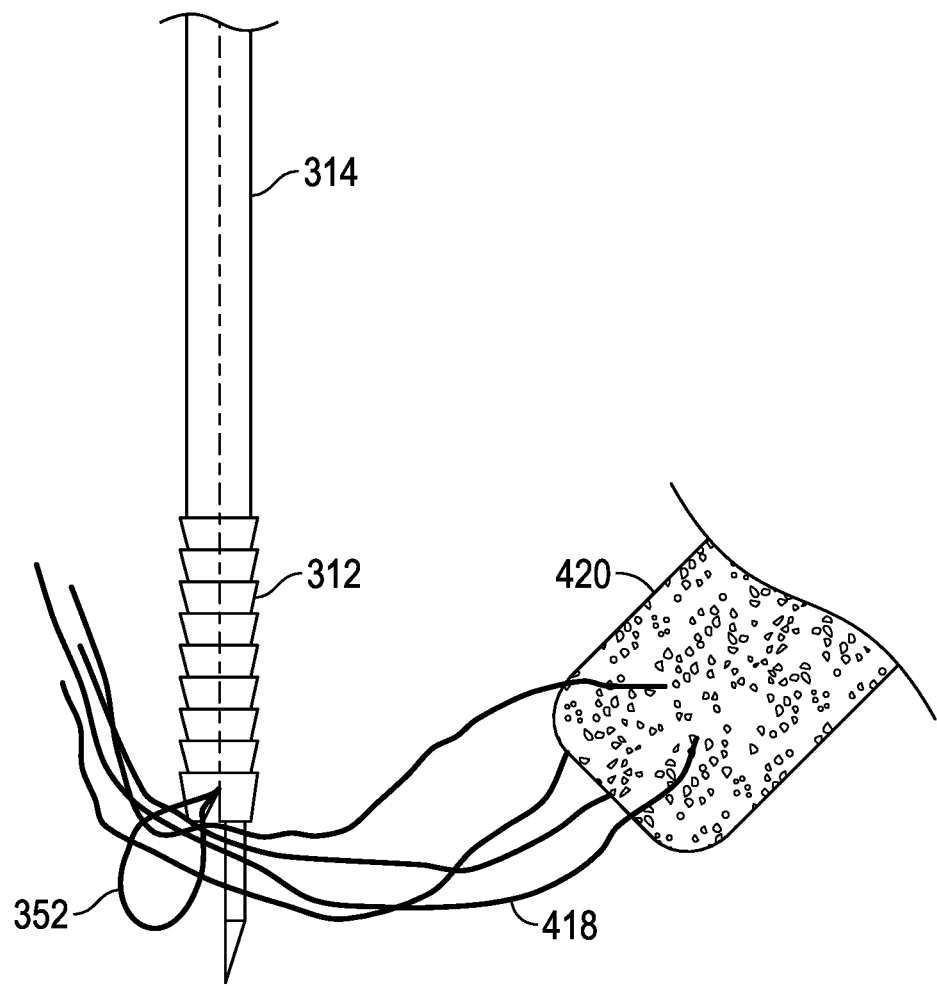
FIGS. 26A-26E are schematic diagrams illustrating use of the suture anchor drive of FIGS. 23 and 24 to implant a suture anchor into a bone.

As shown in FIG. 26A, a suture anchor 312 is positioned onto the drive 314, and a suture loop 352 is shown extending past the leading end 334. The suture loop 352 may be formed by threading or looping a suture through the cannulas 350 and 351 with the free ends of the suture extending from the access opening 362 or 408, for example. Sutures 418 are shown attached to a soft tissue 420 and disposed through the suture loop 352 extending past the leading end 334.

Figure 26B:
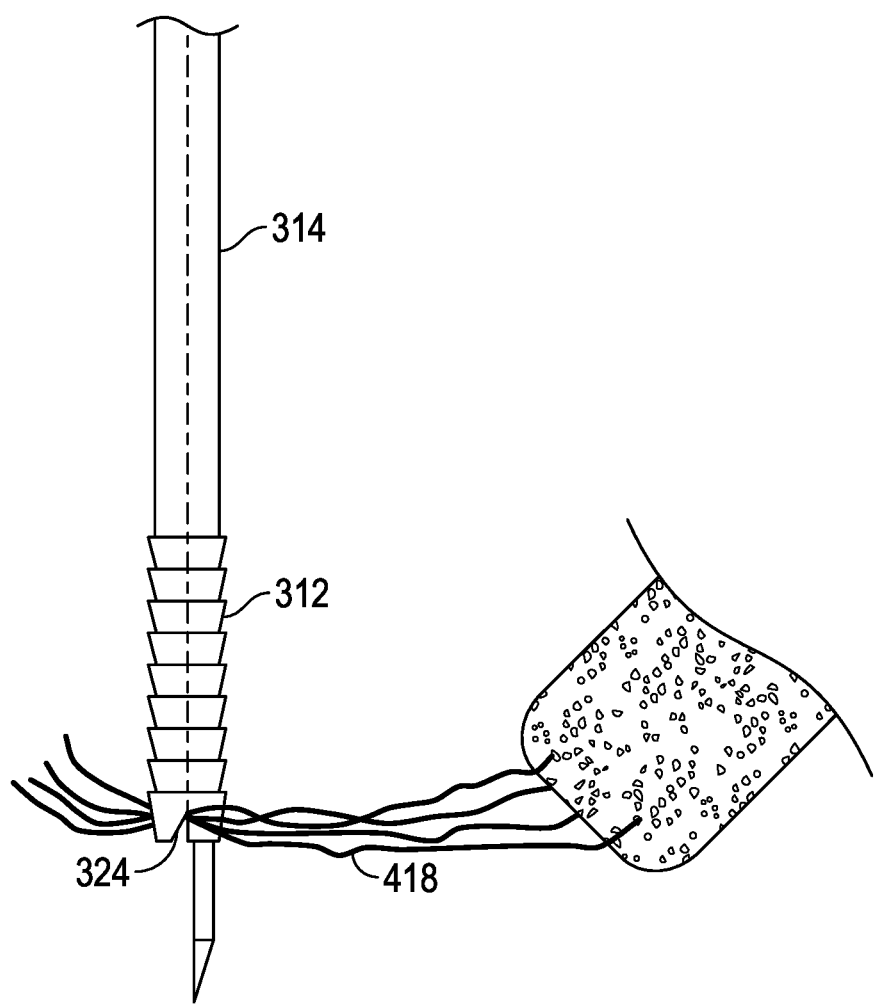

As shown in FIG. 26B, the sutures 418 are positioned in the suture receiving notch 324 of the suture anchor 312 by pulling or retracting the suture loop 352 into the suture anchor 312 and/or the cannula 350 of the rod 328. For example, the portion of the suture loop 352 extending from the cannula access opening 408 may be pulled by the surgeon and secured at any desired tension. In one manner of operation, the sutures 418 traverse the suture anchor 312 with the sutures 418 positioned in opposing portions of the suture receiving notch 324. It is to be understood, however, that a portion of the one or more suture 488 may extend at least partially into the cannula 350.

Figure 26C:
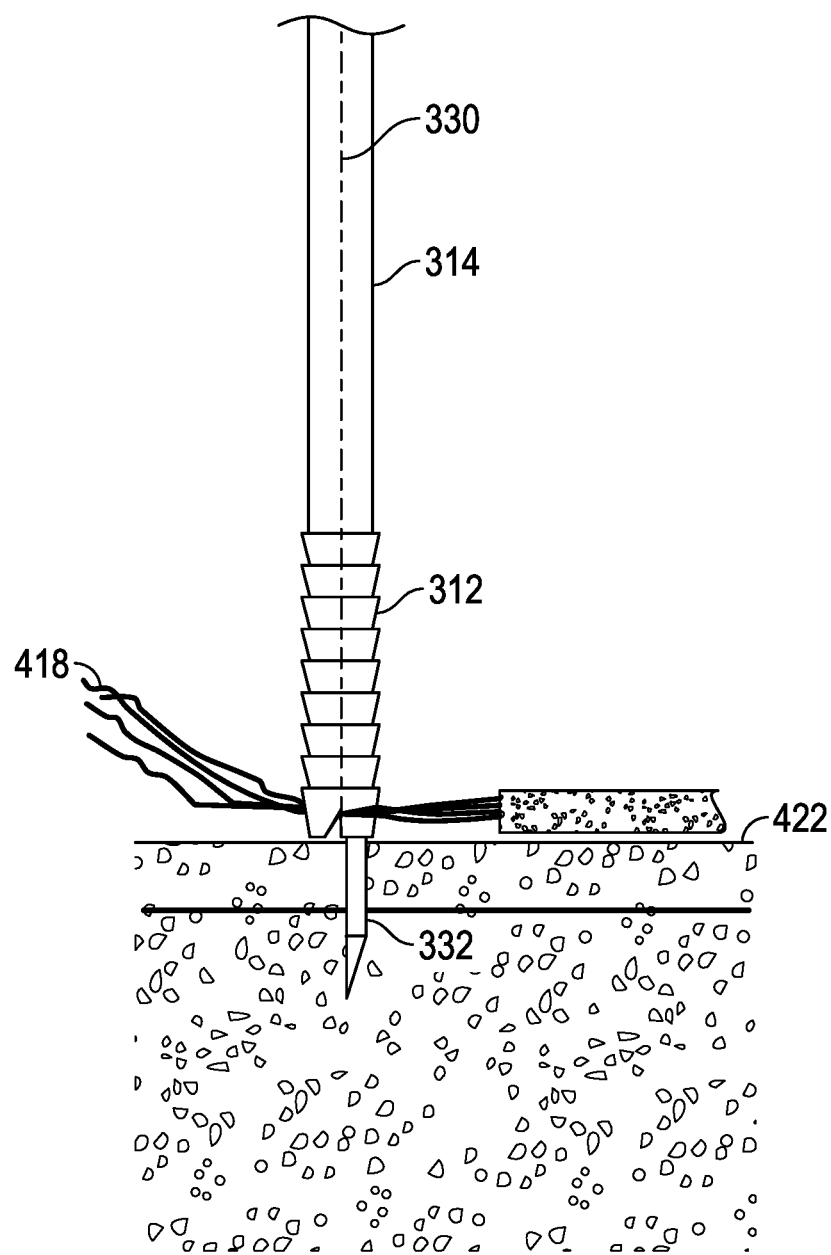

As shown in FIG. 26C, the awl 332 may be used to pierce a bone 422 once a suitable implantation location has been identified and selected by the surgeon, for example. The awl 332 may be driven into the bone 422 in any desired manner, such as manually by the surgeon, by a surgical robot arm, or by impinging an impactor head 348 with a surgical hammer, for example. To form a hole in the bone 422 with the awl 332, the awl 332 may be rotated.

Figure 26D:
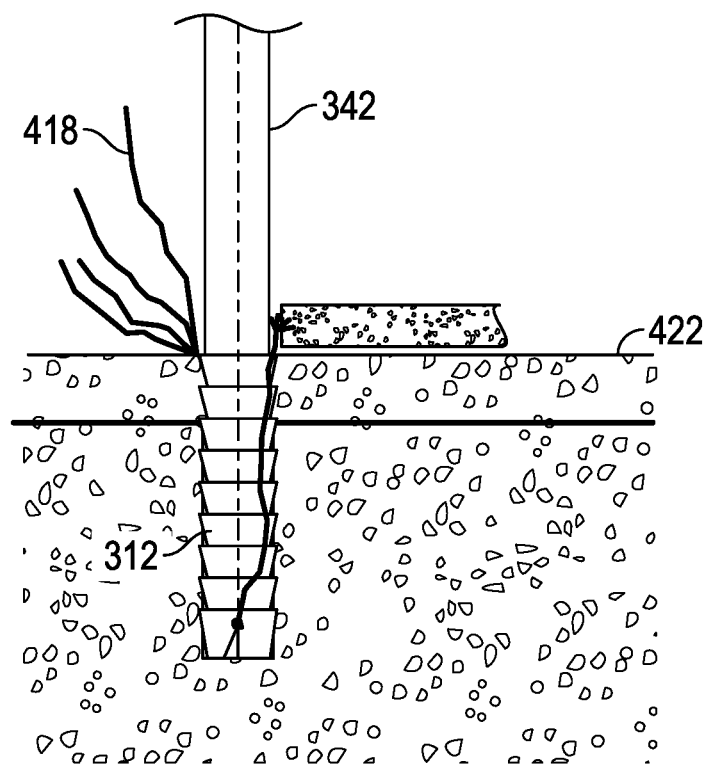

As shown in FIG. 26D, the suture anchor 312 is next driven into the bone 422 by the impactor sleeve 342. As a result, the sutures 418 are transported into the bone by the suture anchor 312.

Figure 26E:
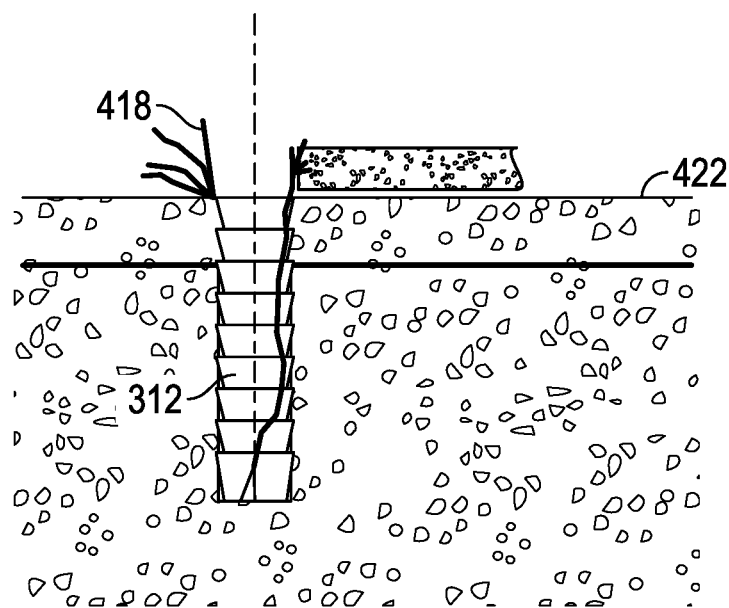

As shown in FIG. 26E, one end of the suture loop 352 may be released so as to allow the suture 352 to be disengaged from the sutures 418, and the awl 332 may then be withdraw from suture anchor 312 leaving the suture anchor 312 implanted in the bone 422. Any excess portions of the sutures 418 may be trimmed or clipped as needed or desired.

It is to be understood that the method described in FIGS. 26A-26E may be modified for implementation with the suture anchor system 380, such as by implementing a suture loop 352 and utilizing the cannula access opening 408 of the suture anchor system 380 similarly to the cannula access opening 362 of the suture anchor system 310 as described with reference to FIGS. 26A-26B above, for example.

As used herein, the terms "patient" is meant to include all organisms, whether alive or dead, including any species having soft tissues and bones. For example, a method according to the inventive concepts disclosed herein may be used to repair a soft tissue detachment injury in a living human, horse, cow, sheep, cat, dog, and the like. In another example, a method according to the inventive concepts disclosed herein may be used in a non-living organism to train medical personnel in surgical techniques. As yet another example, a method according to the instant disclosure may be used to implant medical devices such as replacement joints, pacemakers, and the like, into an organism by anchoring such devices to a bone. As yet another example, a method according to the inventive concepts disclosed herein may be used to repair rotator cuff instabilities and tears in shoulder surgery, or to repair various knee, elbow, hip, wrist, ankle, or other soft tissue detachment and joint injuries.

From the above description, it is clear that the inventive concepts disclosed and claimed herein are well adapted to carry out the objects and to attain the advantages mentioned herein, as well as those inherent in the inventive concepts. While exemplary embodiments of the inventive concepts have been described for purposes of this disclosure, it will be understood that numerous changes may be made which will readily suggest themselves to those skilled in the art and which are accomplished within the spirit of the inventive concepts disclosed and/or as defined in the appended claims.

What is claimed is:

1. A method for anchoring a soft tissue to a bone, comprising:
   supporting a suture anchor on a rod, the rod having a leading end and a trailing end, the leading end defining an awl with at least one point for forming a hole in a bone, the rod having at least one suture holding notch formed near the at least one point, the suture anchor comprising:
      a body member having a leading end, a trailing end, a cannula extending through the body member from the leading end of the body member to the trailing end of the body member, and a threaded outer surface; and
      a tip member having a leading end, a trailing end, and a cannula extending through the tip member from the leading end of the tip member to the trailing end of the tip member, the trailing end of the tip member rotatably connected to the leading end of the body member with the cannula of the tip member axially aligned with the cannula of the body member;
   loading at least one suture into the at least one suture holding notch of the rod;
   selecting an anchoring location on the bone;
   piercing the anchoring location on the bone with the rod so as to cause the rod to carry a portion of the at least one suture into the bone;
   pushing the tip member of the suture anchor into the bone;
   engaging an impactor sleeve with the body member;
   rotating the impactor sleeve to rotate the body member of the suture anchor and sliding the impactor sleeve relative to the rod to threadlingly insert the suture anchor into the bone and cause the suture anchor to slide axially along the rod; and
   removing the rod from the bone thereby leaving the suture anchor and the at least one suture in the bone.

2. The method of claim 1, wherein the leading end of the tip member of the suture anchor has a pair of diametrically opposed suture receiving notches formed therein, and wherein the pair of diametrically opposed suture receiving notches of the suture anchor is aligned with the at least one suture holding notch of the rod as the body member is being threadingly inserted into the bone.

3. The method of claim 1, wherein the impactor sleeve has a leading end with at least one drive protrusion, and wherein the trailing end of the body member has at least one drive receiving notch matingly engaged with the at least one drive protrusion of the impactor sleeve to impart rotation to the body member.

4. The method of claim 3, further comprising grasping a handle connected to the impactor sleeve in a way that the impactor sleeve extends through the handle and is rotatable relative to the handle but longitudinally fixed.

5. The method of claim 4, further comprising retaining a portion of the at least one suture in a notch of a suture fixation collar of the handle as the body member is being threadingly inserted into the bone.

\* \* \* \* \*